(12) United States Patent
Hyde et al.

(10) Patent No.: US 10,307,246 B2
(45) Date of Patent: Jun. 4, 2019

(54) INTRAOCULAR LENS DEVICES, SYSTEMS, AND RELATED METHODS

(71) Applicant: ELWHA LLC, Bellevue, WA (US)

(72) Inventors: Roderick A. Hyde, Redmond, WA (US); Jordin T. Kare, San Jose, CA (US); John Marshall, Farnborough (GB); Clarence T. Tegreene, Mercer Island, WA (US); Roberto Zaldivar, Mendoza (AR); Roger Zaldivar, Mendoza (AR)

(73) Assignee: ELWHA LLC, Bellevue, WA (US)

( * ) Notice: Subject to any disclaimer, the term of this patent is extended or adjusted under 35 U.S.C. 154(b) by 0 days.

(21) Appl. No.: 14/807,719

(22) Filed: Jul. 23, 2015

(65) Prior Publication Data

US 2017/0020660 A1    Jan. 26, 2017

(51) Int. Cl.
*A61F 2/16* (2006.01)

(52) U.S. Cl.
CPC .............. *A61F 2/1627* (2013.01); *A61F 2/16* (2013.01); *A61F 2/1635* (2013.01); *A61F 2/1654* (2013.01); *A61F 2210/009* (2013.01)

(58) Field of Classification Search
CPC .... A61F 2/1627; A61F 2/1635; A61F 2/1654; A61F 2/16; A61F 2210/009
See application file for complete search history.

(56) References Cited

U.S. PATENT DOCUMENTS

| | | | |
|---|---|---|---|
| 5,066,301 A | 11/1991 | Wiley | |
| 5,108,429 A | 4/1992 | Wiley | |
| 5,171,266 A | 12/1992 | Wiley et al. | |
| 5,203,788 A | 4/1993 | Wiley | |
| 5,344,447 A | 9/1994 | Swanson | |
| 6,857,741 B2 | 2/2005 | Blum et al. | |
| 6,871,951 B2 | 3/2005 | Blum et al. | |
| 7,023,594 B2 | 4/2006 | Blum et al. | |
| 7,396,126 B2 | 7/2008 | Blum et al. | |
| 7,475,984 B2 | 1/2009 | Blum et al. | |
| 7,517,083 B2 | 4/2009 | Blum et al. | |
| 7,832,864 B2 | 11/2010 | Barrett et al. | |
| 8,446,341 B2 | 5/2013 | Amirparviz et al. | |
| 8,587,734 B2 | 11/2013 | Li | |
| 8,608,800 B2 | 12/2013 | Portney | |
| 8,885,139 B2 | 11/2014 | Peyghambarian et al. | |
| 2002/0140899 A1 | 10/2002 | Blum et al. | |
| 2003/0210377 A1 | 11/2003 | Blum et al. | |

(Continued)

FOREIGN PATENT DOCUMENTS

| | | | |
|---|---|---|---|
| EP | 2 772 791 A1 | | 9/2014 |
| WO | WO 2009/153764 | * | 12/2009 |
| WO | WO 2014/194432 | * | 12/2014 |

OTHER PUBLICATIONS

PCT International Search Report; International App. No. PCT/US2016/043068; dated Oct. 12, 2016; pp. 1-4.

(Continued)

*Primary Examiner* — Dinah Baria

(74) *Attorney, Agent, or Firm* — Dorsey & Whitney LLP

(57) ABSTRACT

Embodiments disclosed herein are directed to intraocular lens devices, systems, and methods that include determining relative tilt and/or vergence rotation of a subject's eyes and focusing one or more intraocular lenses based on the determined vergence rotation.

45 Claims, 7 Drawing Sheets

(56) References Cited

U.S. PATENT DOCUMENTS

| | | |
|---|---|---|
| 2003/0231293 A1 | 12/2003 | Blum et al. |
| 2004/0027501 A1 | 2/2004 | Blum et al. |
| 2005/0140924 A1 | 6/2005 | Blum et al. |
| 2005/0270481 A1 | 12/2005 | Blum et al. |
| 2006/0098164 A1 | 5/2006 | Blum et al. |
| 2006/0164593 A1 | 7/2006 | Peyghambarian et al. |
| 2007/0121065 A1* | 5/2007 | Cox ................ A61B 3/113 351/209 |
| 2008/0106633 A1 | 5/2008 | Blum et al. |
| 2008/0208335 A1 | 8/2008 | Blum et al. |
| 2009/0009717 A1 | 1/2009 | Barrett et al. |
| 2009/0032679 A1 | 2/2009 | Holladay |
| 2009/0105817 A1 | 4/2009 | Bretthauer et al. |
| 2009/0195749 A1 | 8/2009 | Blum et al. |
| 2010/0001926 A1 | 1/2010 | Amirparviz et al. |
| 2010/0002190 A1 | 1/2010 | Clarke et al. |
| 2010/0225834 A1 | 9/2010 | Li |
| 2010/0324408 A1 | 12/2010 | Klink et al. |
| 2011/0025955 A1 | 2/2011 | Bos et al. |
| 2012/0140167 A1 | 6/2012 | Blum |
| 2013/0035760 A1 | 2/2013 | Portney |
| 2013/0073038 A1 | 3/2013 | Azar |
| 2013/0218270 A1 | 8/2013 | Blanckaert et al. |
| 2013/0222756 A1 | 8/2013 | Van Heugten |
| 2014/0085726 A1 | 3/2014 | Portney |
| 2014/0128941 A1 | 5/2014 | Williams |
| 2014/0132904 A1 | 5/2014 | Bos et al. |
| 2014/0156000 A1 | 6/2014 | Campin et al. |
| 2014/0240656 A1 | 8/2014 | Pugh et al. |
| 2015/0057748 A1 | 2/2015 | Azar |
| 2015/0205126 A1 | 7/2015 | Schowengerdt |
| 2015/0362749 A1 | 12/2015 | Biederman et al. |

OTHER PUBLICATIONS

PCT International Search Report; International App. No. PCT/US2016/043065; dated Nov. 4, 2016; pp. 1-3.

PCT International Search Report; International App. No. PCT/US2016/043062; dated Oct. 21, 2016; pp. 1-3.

European Patent Office, Extended European Search Report, Pursuant to Rule 62 EPC; App. No. EP 16828438.8; dated Feb. 28, 2019 (received by our Agent on Mar. 11, 2019); pp. 1-8.

European Patent Office, Extended European Search Report, Pursuant to Rule 62 EPC; App. No. 16828440.4; dated Feb. 22, 2019 (received by our Agent on Mar. 5, 2019); pp. 1-9.

* cited by examiner

INTRAOCULAR LENS DEVICES, SYSTEMS, AND RELATED METHODS

RELATED METHODS

If an Application Data Sheet (ADS) has been filed on the filing date of this application, it is incorporated by reference herein. Any applications claimed on the ADS for priority under 35 U.S.C. §§ 119, 120, 121, or 365(c), and any and all parent, grandparent, great-grandparent, etc. applications of such applications, are also incorporated by reference, including any priority claims made in those applications and any material incorporated by reference, to the extent such subject matter is not inconsistent herewith.

CROSS-REFERENCE TO RELATED APPLICATIONS

The present application claims the benefit of the earliest available effective filing date(s) from the following listed application(s) (the "Priority Applications"), if any, listed below (e.g., claims earliest available priority dates for other than provisional patent applications or claims benefits under 35 USC § 119(e) for provisional patent applications, for any and all parent, grandparent, great-grandparent, etc. applications of the Priority Application(s)).

PRIORITY APPLICATIONS

None.

If the listings of applications provided above are inconsistent with the listings provided via an ADS, it is the intent of the Applicant to claim priority to each application that appears in the Domestic Benefit/National Stage Information section of the ADS and to each application that appears in the Priority Applications section of this application.

All subject matter of the Priority Applications and of any and all applications related to the Priority Applications by priority claims (directly or indirectly), including any priority claims made and subject matter incorporated by reference therein as of the filing date of the instant application, is incorporated herein by reference to the extent such subject matter is not inconsistent herewith.

BACKGROUND

Intraocular lenses (IOLs), such as pseudophakic IOLs, aphikic IOLs, or phakic IOLs (PIOLS), can be used to correct the vision of a subject. Typical IOLs can include monofocal, multifocal, or accommodative configurations. IOLs can include an optic element (e.g., lens) and haptic elements (e.g., arms or wings configured to aid in positioning the IOL).

Such configurations can be limited to focusing either on near or far vision without selectively modifiable adjustment therebetween. Therefore, manufacturers, users, and designers of IOLs continue to seek improved IOLs.

SUMMARY

Embodiments disclosed herein are directed to IOL devices, IOL systems, and methods that include determining relative tilt and/or vergence rotation of a subject's eyes and focusing one or more intraocular lenses responsive to the determined vergence rotation. In an embodiment, an IOL system can include at least one IOL device that can be positioned in an eye of a subject, a sensor that can provide or generate an output related to the vergence rotation of the subject's eyes, and a controller that can direct the IOL device to change focal length. For example, the IOL system can include a field source that can establish an identifiable field that can be sensed or detected by the sensor. In an embodiment, the sensor and the identifiable field can have relative locations such that change in vergence between the eyes (e.g., vergence rotation of the eyes) of the subject produces a change in relative positions and/or orientations between the sensor and the identifiable field. For example, as the eyes of the subject tilt or pivot, the sensor and the identifiable field can move relative to each other, and the detected changes in the field can be related to a vergence rotation between the eyes of the subject.

An embodiment includes an IOL system. The IOL system includes a magnetic field source sized and configured to be placed in a first eye of a subject. The magnetic field source is configured to establish an identifiable magnetic field having a predetermined orientation relative to the first eye. The IOL system also includes an IOL device sized and configured to be placed in a second eye of the subject. The IOL device includes a switchable lens configured to selectively switch between a first focal length and at least a second focal length that is less than the first focal length. The IOL device further includes a sensor configured to detect a change in the established identifiable magnetic field corresponding to a vergence rotation between the first eye and the second eye. The sensor is configured to generate one or more detection outputs at least partially based on the detected change. The IOL device further includes a controller operably coupled to the sensor to receive the one or more detection outputs therefrom. The controller includes control electrical circuitry configured to direct the switchable lens to selectively switch between the first focal length and the at least a second focal length responsive to the one or more detection outputs.

An embodiment includes a method of adjusting a focal length of one or more intraocular lens devices. The method includes establishing an identifiable magnetic field with a magnetic field source positioned in a first eye of the subject. The identifiable magnetic field has a predetermined orientation relative to the first eye. The method also includes, at a controller, receiving one or more detection outputs from a sensor. The one or more detection outputs based on a detected change in the established identifiable magnetic field corresponding to a vergence rotation between the first eye and a second eye of the subject. The method further includes, responsive to at least the one or more detection outputs, modifying the focal length of one or more intraocular lens devices positioned in one or more of the first eye or the second eye.

An embodiment includes an IOL system. The IOL system includes a magnetic field source configured to be positioned on a subject. The magnetic field source is configured to establish an identifiable magnetic field having a predetermined orientation relative to the first eye. The IOL system also includes a sensor configured to detect a change in the established identifiable magnetic field at least partially corresponding to a vergence rotation between the first eye and a second eye of the subject. The sensor is configured to generate one or more detection outputs on the detected change. The system further includes an IOL device sized and configured to be placed in the second eye of the subject. The IOL device includes a switchable lens configured to selectively switch between a first focal length and at least a second focal length that is less than the first focal length. The IOL device also includes a controller operably coupled to the sensor to receive the one or more detection outputs therefrom. The controller includes control electrical circuitry configured to direct the switchable lens to selectively switch between the first focal length and the second focal length responsive to the one or more detection outputs.

Features from any of the disclosed embodiments can be used in combination with one another, without limitation. In addition, other features and advantages of the present disclosure will become apparent to those of ordinary skill in the art through consideration of the following detailed description and the accompanying drawings.

The foregoing summary is illustrative only and is not intended to be in any way limiting. In addition to the illustrative aspects, embodiments, and features described above, further aspects, embodiments, and features will become apparent by reference to the drawings and the following detailed description.

DETAILED DESCRIPTION

Figure 2:
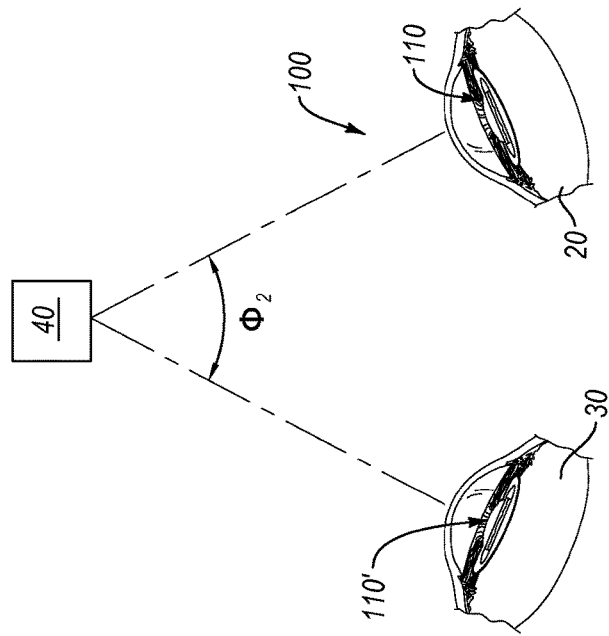
FIG. 2 is a schematic top view of the subject's eyes of FIG. 1, with the eyes having a second vergence therebetween and are focused on a second object at a second distance from the subject that is less than the first distance according to an embodiment.

Embodiments disclosed herein are directed to IOL devices, IOL systems, and methods that include determining relative tilt or vergence rotation of a subject's eyes and focusing one or more intraocular lenses based on the determined vergence rotation. In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments can be utilized, and other changes can be made, without departing from the spirit or scope of the subject matter presented here.

In one or more embodiments, the IOL system can include at least one IOL device that can be positioned in an eye of a subject, a sensor that can provide or generate an output related to a vergence rotation of the subject's eyes, and a controller that can direct the IOL device to change focal length responsive to the output related to the vergence rotation. For example, the IOL system can include a field source that can establish an identifiable field that can be sensed or detected by the sensor. In an embodiment, the sensor and the identifiable field can have relative locations such that a change in vergence between the eyes (e.g., vergence rotation of the eyes) of the subject produces a change in relative positions or orientations between the sensor and the identifiable field. For example, as the eyes of the subject tilt or pivot, the sensor and the identifiable field can move relative to each other, and the detected changes in the field can be related to a vergence rotation between the eyes of the subject.

In an embodiment, the field can be an identifiable magnetic field established by a permanent or electromagnet. Furthermore, as discussed below in more detail, the field source (e.g., a magnetic field source) can be positioned in at least one eye of the subject. For example, the field source can be embedded in or mounted to an IOL device that can be located in one of the subject's eye. Alternatively or additionally, the field source can be positioned near, but externally to one or both of the subject's eyes. In an embodiment, one or more sensors positioned in one or both eyes of the subject can detect a change in the identifiable field or in a component thereof, during vergence rotation (e.g., as the vergence between the eyes changes), such as when the eyes converge or diverge. Hence, for example, the detected change in an identifiable magnetic field or a component thereof can correspond to a change in the vergence between the eyes.

As mentioned above, the IOL system can include a controller. For example, the controller can be operably coupled to the sensor and can receive detection output from the sensor. More specifically, the detection output from the sensor can be based on the detected change in the field or based on the one or more components thereof, which can be related to vergence rotation between the eyes of the subject. In an embodiment, the control can distinguish between vergence rotation of the eyes and co-tilt rotation of the eyes (e.g., when the eyes of the subject tilt in the same direction, such as to view an object located peripherally or to a side of the subject). As a consequence of such distinguishing, in such embodiments each IOL can act independently of the other, reaching an accurate vergence determination (and hence an accurate focal length determination) on its own, without a need for communication between both IOLs so as to compare each IOL's determined tilt with that of the other IOL in order to decide which portion of each IOL's tilt represents vergence and which represents co-tilt.

In an embodiment, the IOL device can be switchable between two or more focal lengths (e.g., a first focal length for distance vision and a second focal length for close-up vision). For example, the IOL device can include one or more switchable lenses that can be directed or switched between two or more focal lengths by the controller. Moreover, the controller can be operably connected to the sensor(s) and can receive outputs therefrom, which can be related to the detected change in the field and, hence, to vergence rotation between the eyes. In an embodiment, the controller can switch or direct switching of the IOL device at least partially based on the outputs received from the sensor(s).

In an embodiments, the IOL systems disclosed herein can include one or more sensors configured to detect one or more physiological indicia of the subject. For example, the IOL system can include one or more sensors configured to detect glucose concentration, such as in the eye of the subject; eye pressure, heart rate, biological proteins present in the eye, or any other biological indicia. The one or more sensors can be operably coupled to the controller. The controller of the IOL system can be configured to transmit the measurements of the physical indicia to a remote source such as a computer, a cellular phone, or other electronic device. In an embodiment, the measured physical indicia may be used to determine the health of a subject or eye thereof, customize the operation of the IOL device to the particular subject, determine if the IOL controller needs to be removed or adjusted, or determine if the focal adjustments of the IOL controller are suitable for the subject. The electronic device may then transmit instructions to the controller to selectively control or otherwise adjust the functioning of the IOL system, such as controllably changing the focal length of the IOL device.

Figure 1:
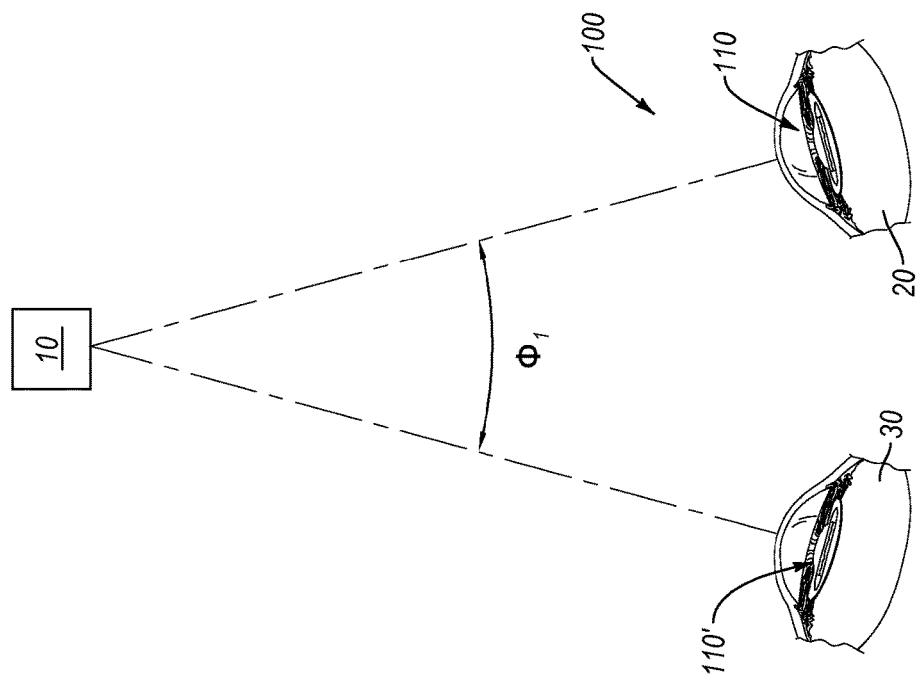
FIG. 1 is a schematic top view of a subject's eyes having a first vergence therebetween and focused on a first object at a first distance from the subject according to an embodiment.

FIG. 1 schematically illustrates eyes 20 and 30 of a subject focused on a first object 10 that is positioned at a first distance from the subject. In particular, when the eyes 20, 30 are focused on the first object 10, an angle between respective optical axes thereof can be at a vergence angle $\phi_1$. FIG. 1 also schematically illustrates an IOL system 100 according to an embodiment. For example, an IOL system 100 can include a first IOL device 110 positioned in a first eye 20 and a second IOL device 110' positioned in a second eye 30 of the subject.

Generally, the first IOL device 110 or the second IOL device 110' can be configured to augment or correct visual deficiencies of the subject or to replace the lenses in the respective first eye 20 or second eye 30 of the subject (e.g., in cataract surgeries). It should be appreciated that, in one or more embodiments, the IOL system 100 can include only a single IOL device (e.g., the first IOL device 110 or the second IOL device 110'), which can be positioned in the first eye 20 or in the second eye 30. The IOL devices 110 or 110' can be switched to or set at a first focal length, such that the light entering the eye from the distance of the first object 10 is focused on the retina of the respective eyes 20, 30, thereby focusing the eyes 20, 30 on the first object 10.

When the subject focuses on another object, such as an object that is closer to the subject than the first object 10, the object's eyes 20, 30 can tilt such as to converge, thereby changing the angle between the optical axes thereof. FIG. 2 schematically shows the subject's eyes 20, 30 focused on a second object 40, which is positioned at a second distance and closer to the subject than the first object 10 (FIG. 1). For example, when the eyes 20, 30 focus on the second object 40, the angle between the optical axis thereof can change to a second angle $\phi_2$. More specifically, as the eyes 20, 30 focus on the closer, second object 40, the eyes 20, 30 converge or in-tilt, such that the second angle $\phi_2$ defined by the respective optical axis thereof is greater than the first angle $\phi_1$.

In an embodiment, responsive to the changed tilt between the eyes 20, 30, the IOL devices 110 or 110' can be switched to the second focal length, which can be shorter than the first focal length. The IOL devices 110 or 110' can include one or more sensors that can sense or detect a change in an identifiable field (e.g., magnetic field) and can correlate that change to the change vergence rotation between the eyes 20, 30 (e.g., convergence to focus on a closer object or divergence to focus on a farther object). Similarly, as the subject attempts to focus eyes 20, 30 on an object at a distance that is greater than the distance to the second object 40 (e.g., on the first object 10 (FIG. 1)), the IOL devices 110 or 110' can be switched to the first focal length (longer than the second focal length).

Moreover, as described below in more detail, the IOL devices 110 or 110' can distinguish between vergence rotation from co-tilt rotation (e.g., when the eyes 20, 30 rotate in the same direction, such as to observe an object located peripherally from the user). As such, for example, the IOL device 110 or 110' can switch focal length responsive to detected vergence rotation. In an embodiment, the IOL devices 110 or 110' can maintain a previously set focal length during co-tilt of the eyes 20, 30.

Figure 3:
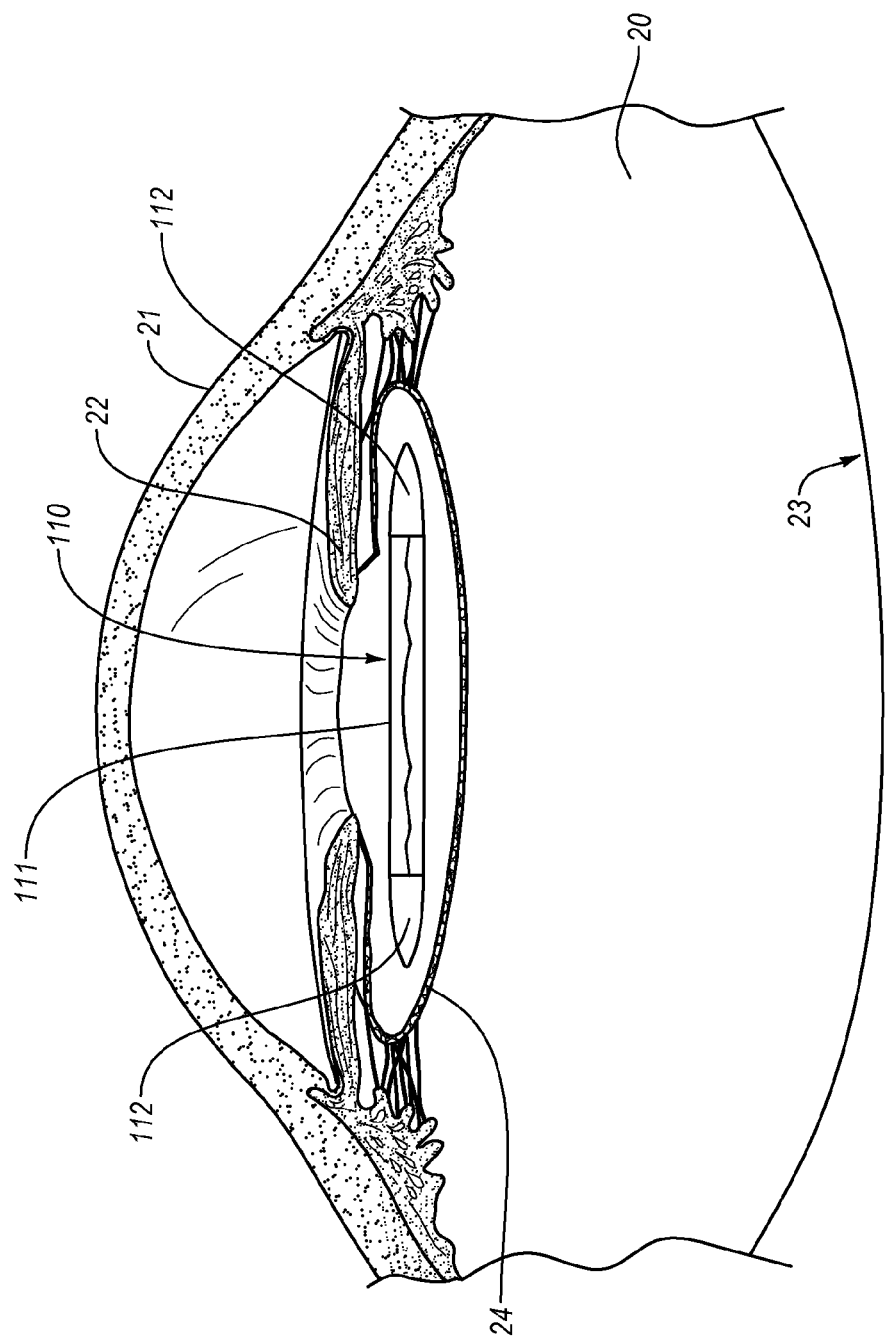
FIG. 3 is a schematic, side, cross-sectional view of a subject's eye and an intraocular lens device located in the eye according to an embodiment.

As mentioned above, the IOL devices 110 or 110' can be located in the subject's eyes (e.g., in the eye 20 or in the eye 30). FIG. 3 is a side, cross-sectional view of the eye 20 with the IOL device 110 implanted therein, according to an embodiment. It should be appreciated that, while the description herein is related to the IOL device 110 and to the corresponding eye 20 of the subject, the IOL device 110' or its location in the eye 30 (FIGS. 1-2) can have the same or similar configuration. Generally, the eye 20 includes a cornea 21, an iris 22, a natural lens, and a retina 23 therebehind. One or more IOL device 110 can be implanted in the eye 20. For example, the IOL device 110 can be implanted over the natural lens, in front of (e.g., in the anterior chamber) or behind the iris 22 (e.g., in the posterior chamber), or internal to the natural lens such as in a capsular bag 24 of the natural lens. In an embodiment, the natural lens can be absent from the eye 20 (e.g., the IOL device 110 can replace the natural lens and can be placed in the anterior chamber, the posterior chamber, or internal to the capsular bag that is used to contain the natural lens).

Generally, as described below in more detail, the IOL device 110 can include a lens 111 and haptics 112 connected to or integrated with the lens 111. In an embodiment, the haptics 112 can be positioned on or secured to one or more structures in the eye 20, thereby positioning or securing the IOL device 110 in the eye 20. For example, the haptics 112 can be positioned on the ciliary body or muscles or in or on the capsular bag 24 of the natural lens. The lens 111 can be located laterally in the center of the eye 20 with the haptics 112 extending laterally therefrom. As mentioned above, the lens 111 of the IOL device 110 can be switched between two or more focal lengths, to focus light entering the eye from a selected distance on the retina 23 of the eye 20, thereby providing a focus on an object located at the selected focal length and augmenting or correcting the vision of the subject.

In an embodiment, the IOL device 110 can be substantially fixed within the eye 20 (e.g., the IOL device can be substantially immobile relative to the optical axis of the eye 20). As such, for example, movement of the eye 20 can result in a corresponding movement of the IOL device 110. In particular, as the eye 20 tilts or pivots in the eye socket, the IOL device 110 can correspondingly tilt or pivot together with the eye 20. Furthermore, one, some, or all of the elements or components of the IOL device 110 can have a predetermined orientation relative to the eye 20 or relative to the optical axis thereof, as described below in more detail.

Figure 4A:
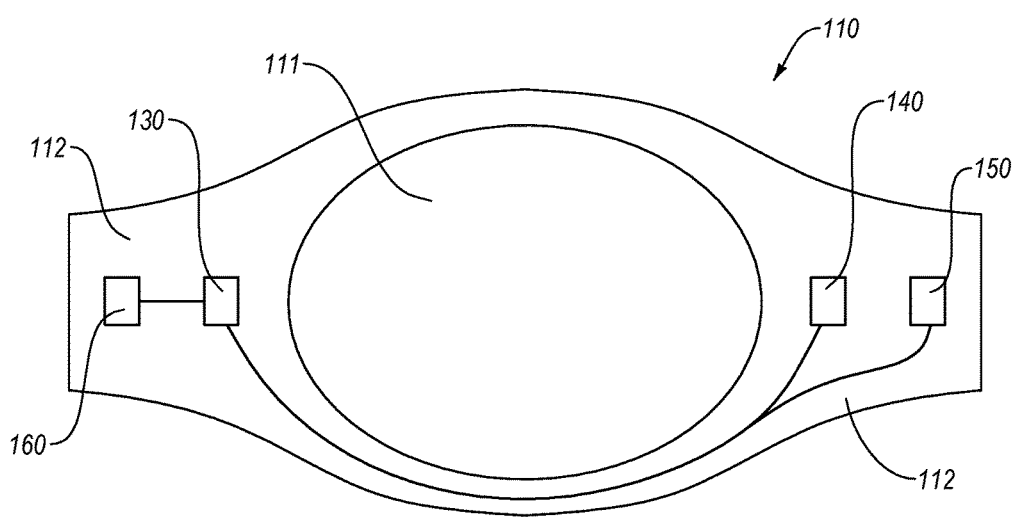
FIG. 4A is a top view of an IOL device located in the eye according to an embodiment.
Figure 4B:
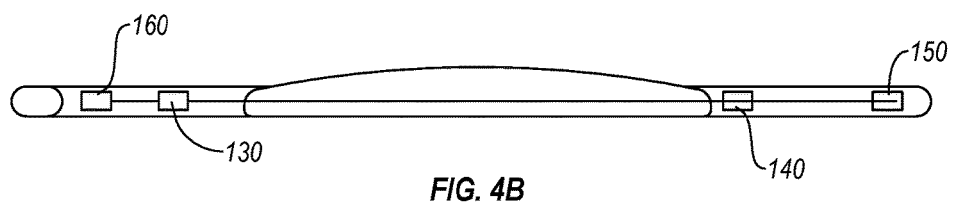
FIG. 4B is a side view of the IOL device of FIG. 4A.

FIGS. 4A and 4B illustrate the IOL device 110 according to an embodiment. FIG. 4A is a top view of the IOL device 110 and FIG. 4B is a side view of the IOL device 110. As described above, the IOL device 110 can be configured to fit in or on one or more anatomical structures of the eye and can include the lens 111 and one or more haptics 112. As shown in FIG. 4A, in an embodiment, the IOL device 110 includes the lens 111. For example, the lens 111 can be configured to focus light onto the surface of the retina and can be substantially circular or elliptical. Furthermore, the lens 111 can be switchable between two or more focal lengths and, in an embodiment, three or more focal lengths.

In an embodiment, the lens 111 can include or can be configured as a switchable diffractive lens. Additionally or alternatively, the lens 111 can include or can be configured as a refractive lens that can have a selectively modifiable index of refraction and focal length (e.g., a variable focus refractive lens). In any embodiment, the lens 111 can be switched at least between the first focal length and at least a second focal length.

In an embodiment, a controller including control electrical circuitry can be operably coupled to the lens 111 and can switch or direct switching of the lens 111 between two or more focal lengths. In an embodiment, the controller can be positioned on or embedded in one or more portions of the IOL device 110. For example, a controller 130 can be mounted on or embedded in the haptics 112 (as shown in FIG. 4B), in the lens 111 of the IOL device 110, or in another part of the IOL device 110. Moreover, the controller 130 can receive a detection output from a sensor; the detection output can be related or correspond to the vergence rotation between the subject's eyes. At least partially based on the received detection output, the controller 130 can switch the lens 111 to a suitable or predetermined focal length.

For example, the controller 130 can be operably coupled to and can receive a detection output from a sensor 140 that can be positioned on or embedded in one or more portions of the IOL device 110. For example, the sensor 140 can be mounted on or embedded in the haptics 112 (as shown in FIG. 4B) or in the lens 111 of the IOL device 110. Generally, the sensor 140 can be any suitable sensor for detecting changes in the identifiable field, which can correspond to vergence rotation of the eyes, as described below in more detail.

In an embodiment, the identifiable field can be an identifiable magnetic field. Hence, for example, the sensor 140 can be a magnetic field sensor. Generally, the sensor 140 can be any suitable sensor or multiple sensors, which can be sufficiently miniaturized and can be configured for placement in the subject's eye (e.g., MEMS-based sensors that can be embedded in or mounted on one or more portions of the IOL device 110). Examples of suitable sensors include Hall effect sensors, magnetoresistance sensors (e.g., AMR magnetometer, GMR magnetometer), induction coils, magneto-diodes, Lorentz force based sensors, an electron tunneling based sensor, or a MEMS compass. For example, the sensor 140 can generate a detection output (e.g., a measurable change in voltage or resonant frequency) that can be related to or based on the changes in the position of an identifiable magnetic field, which can be related to the change in vergence between the subject's eyes. In an embodiment, the sensor 140 can generate a signal that can include detection output of the sensor 140.

In an embodiment, the IOL device 110 can include a field source 150 (e.g., a magnetic field source), which can establish an identifiable magnetic field that can be detectable by an additional sensor that can be operably coupled to an additional controller. The field source 150 can be a dipole magnet (e.g., a permanent magnet, an electromagnet, or combination of the foregoing) and can establish or generate a corresponding identifiable dipole magnetic field. Furthermore, the field source 150 can be mounted on or embedded in the IOL device 110. For example, the field source 150 can be embedded in the haptics 112 (as shown in FIG. 4B) or in the lens 111 of the IOL device 110.

In an embodiment, the field source 150 can be generally fixed in or stationary relative to the eye. Additionally or alternatively, the field source 150 can have a predetermine orientation relative to the eye or to the optical axis thereof. For example, the field source can be embedded within the IOL device 110 at a first predetermined orientation relative to the IOL device 110, and the IOL device 110 can be implanted within the eye at a second predetermined orientation relative to the eye. As such, for example, the identifiable field, such as an identifiable magnetic field can have a predetermined orientation relative to the eye or relative to the optical axis thereof.

Moreover, in an embodiment, the IOL device 110 can be positioned in the eye in a manner that movement of the eye results in a corresponding movement of the IOL device 110. Hence, for example, movement of the eye can produce a corresponding movement of the field source 150 and of the magnetic field established thereby. As such, a sensor detects the change in the established identifiable magnetic field, which can correspond to the movement of the identifiable magnetic field and of the eye (e.g., the movement of the eye can be tilting or pivoting of the eye that at least partially corresponds to a vergence rotation between the eyes).

The IOL device(s) can be located in one or in both eyes of the subject. In an embodiment, an IOL device in the first eye can communicate with another IOL in the second eye, and vice versa (e.g., the IOL devices can be operably coupled together). For example, the IOL device in the second eye can send to the IOL device 110 in the first eye the detection output received from a first sensor in the IOL in the second eye, can send focal length determination, etc. In an embodiment, the IOL device 110 can include a communication device 160 (e.g., the controller 130 can be operably coupled to the communication device 160). The communication device 160 can be mounted on or embedded in the IOL device 110. For example, the communication device 160 can be embedded in the haptics 112 (as shown in FIG. 4B) or in the lens 111 of the IOL device 110.

The communication device 160 can be wireless (e.g., the communication device 160 can be a transmitter or a transceiver) or wired. For example, a wireless (e.g., RF-based or US-based) connection can be established between the communication device 160 and another or additional communication device. Alternatively, the communication device 160 and another communication device can have a wired connection therebetween. For example, an electrical conductor connecting the communication device 160 and another communication device can be implanted in or near the eyes of the subject. In any embodiment, the communication device 160 can be operably coupled to the additional communication device, such as to send data therebetween.

In an embodiment, the controller 130, sensor 140, field source 150, or communication device 160 can be operably coupled or connected to a power source. For example, the power source can include a rechargeable energy storage device or battery (not shown) that can be mounted on or embedded in the IOL device 110. The battery can be wirelessly recharged (e.g., a wireless or inductive charger can recharge the battery). In an embodiment, the battery can be operably connected to a photovoltaic cell that can be mounted on or embedded in the IOL device 110. Alternatively or additionally, the battery can be operably connected or coupled to a charge port that can be configured to accept a charging device. In any event, the power source can power one or more of the controller 130, sensor 140, field source 150, or communication device 160.

In an embodiment, the power source may include a parasitic power device, such as an induction coil, one or more photocells, thermoelectric device, or any other device configured to harvest energy from a subject or the environment. For example, the induction coil can include a channel having a magnet therein, the channel passing the induction coil upon movement of the subject (e.g., eye-movement or blinking) In an embodiment, an induction coil can be disposed in the eye of a subject (e.g., in or adjacent to the IOL) and a corresponding magnet may be positioned on an adjacent part of the subject (e.g., an eyelid or bridge of the nose) whereby movement of the eye or eyelid can cause a current in the induction coil.

Again, while the IOL device 110 is described as including the controller 130, sensor 140, field source 150, and communication device 160, configurations of the IOL device 110 can vary from one embodiment to the next. In particular, for example, the IOL device 110 can include only the controller 130 and sensor 140, and the sensor 140 can detect a change in the identifiable field (e.g., identifiable magnetic field) established by the field source positioned externally to the IOL device 110 or to the eye in which the IOL device 110 is located (e.g., the field source can be located in another eye, can be implanted near the eyes, such as on a nose, can be wearable, etc.). In an embodiment, the IOL device 110 can include only the field source 150, and as the eye together with the IOL device 110 tilt or pivot, a sensor in the second eye can detect the change in the identifiable magnetic field that is established by the field source 150 (e.g., another IOL device in the second eye can include a sensor operably coupled to a controller).

As described above, the IOL system can include a single IOL device or multiple IOL devices (e.g., an IOL device can be located in one or in both eyes of the subject). Generally, the IOL devices of the IOL system can be similar to or the same as the IOL device 110. It should be appreciated, however, that any of the IOL devices included in the IOL systems described herein can include or can be operably coupled to any number of controllers, sensors, field sources, communication devices, or combinations thereof, which can be similar to or the same as the controller 130, sensor 140, field source 150, and communication device 160.

FIGS. 5A-5D schematically illustrate an IOL system 100*a* that includes a first IOL device 110*a* in the first or right eye (not shown), and a second IOL device 110*b* in the second or left eye (not shown), according to an embodiment. It should be appreciated that designations, first eye/right eye and second eye/left eye are used for ease of description only and should not be read as limiting (e.g., the first IOL device 110*a* can be positioned in the second or left eye and the second IOL device 110*b* can be positioned in the first or right eye). Except as otherwise described herein, the first IOL device 110*a*, second IOL device 110*b*, and their elements and components can be similar to or the same as the IOL device 110 (FIGS. 3-4B) and its corresponding elements and components.

Figure 5A:
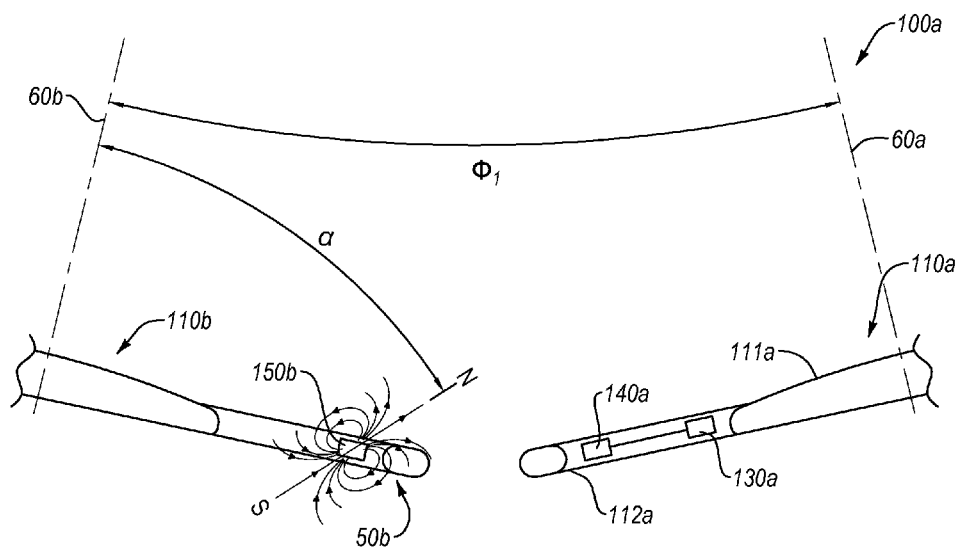
FIG. 5A is a schematic top view of an IOL system that includes two IOL devices oriented by the subject's eyes at a first vergence therebetween according to an embodiment.

FIG. 5A illustrates the first IOL device 110*a* and the second IOL device 110*b*, with respective first and second optical axes 60*a* and 60*b* of the first and second eyes oriented to define a first angle $\phi_1$ therebetween, at which the eyes are focused on first object at first distance from the subject. In an embodiment, the first IOL device 110*a* includes a sensor 140*a* operably coupled to a controller 130*a* including control electrical circuitry (e.g., the sensor 140*a* or controller 130*a* can be embedded in the first IOL device 110*a*, such as in the haptics 112*a* of the first IOL device 110*a*). Moreover, the controller 130*a* can be operably coupled to first lens 111*a* of the first IOL device 110*a*, such as to switch or direct switch of the focal length of the first lens 111*a* at least between to different focal lengths.

In an embodiment, the second IOL device 110*b* can include a magnetic field source 50*b* mounted thereon or embedded therein. The magnetic field source 150*b* can establish an identifiable magnetic field 50*b* that can be sensed by the sensor 140*a*. More specifically, for example, the sensor 140*a* can detect the change in orientation or location of the identifiable magnetic field 50*b*. It should be also appreciated that the magnetic field source 50*b* can be positioned or secured in the subject's second eye without the second IOL device 110*b* (e.g., the magnetic field source 50*b* can be implanted in the eye, such as in the sclera of the eye). In any event, in one or more embodiments, the magnetic field source 150*b* can move and tilt together with the second eye (correspondingly moving the identifiable magnetic field 50*b*), and the sensor 140*a* can detect the change in the orientation or location of the identifiable magnetic field 50*b*. It should be also appreciated that any of the elements or components described herein as included in one or more IOL devices can be directly implanted in the eye, without implanting an IOL device in that eye (e.g., a second, a controller, etc., can be implanted in the eye).

In an embodiment, the controller 130*a* is configured to correlate the detected change in the identifiable magnetic field 50*b* with the vergence rotation between the eyes. For example, the sensor 140*a* can generate a detection output that can correspond to a change at least partially corresponding to the vergence rotation by detecting a changed component of the identifiable magnetic field, which can be in a direction substantially perpendicular to a direction of a dominant component of the identifiable magnetic field. Furthermore, the detection output can be received by the controller 130*a*, and based on the detection output, the controller 130*a* can determine the vergence rotation between the eyes.

In an embodiment, at least partially based on or from the vergence rotation, the controller 130*a* can determine an apparent object distance (e.g., the distance from the subject to the object on which the subject's eyes are attempting to focus). In an embodiment, at least partially based on the determined distance, the controller 130*a* can determine the first or second focal length for the switchable lens (e.g., for the switchable lens 111*a* or for the switchable lens of the second IOL 110*b*) and can switch or direct switch of the switchable lens to the determined focal length.

Generally, the magnetic field source 50*b* can be any suitable magnet, which can establish any suitable magnetic field that can vary from one embodiment to the next. In the illustrated embodiment, the magnetic field source 50*b* is a dipole magnet, such as a permanent magnet (e.g., a ferromagnet). In an embodiment, the magnetic field source 50*b* can be a dipole electromagnet. In an embodiment, the magnetic field source 50*b* can generate a magnetic field having both a dipole and a non-dipole contribution. In such an embodiment, the non-dipole contributions generally weaken more with distance from the magnetic field source 50b than do the dipole contributions so that at a sufficient distance from the magnetic field source 50b (e.g., at the sensor location 140a), the dominant contribution is that of a magnetic dipole. In an embodiment, the electromagnet can be operably coupled to the controller 130a or to an additional controller (e.g., to a controller in the second IOL device 110b), which can turn on or off the electromagnet or can change an intensity of the magnetic field established or generated thereby. For example, the electromagnet can be pulsed in a manner that can distinguish or identify the magnetic field established thereby from other, interfering magnetic fields that can be present in the subject's environment. Moreover, based on the detection output from the sensor 140a, the controller 130a can distinguish the identifiable pulsed magnetic field from other magnetic fields.

Generally, as mentioned above, the sensor 140a can be any suitable sensor or multiple sensors, which can be sufficiently miniaturized for placement in the subject's eye (e.g., MEMS based sensors that can be embedded in or mounted on the first IOL device 110a). Examples of suitable sensors include Hall effect sensors, magnetoresistance sensors (e.g., AMR magnetometer, GMR magnetometer), induction coils, magneto-diodes, Lorentz force based sensors, Electron Tunneling based sensor, MEMS compass, etc. In any event, the sensor 140a can be or can include any suitable sensor or combination of sensors that can detect the change in the location or orientation of the identifiable magnetic field 50b.

In an embodiment, the first IOL device 110a can be positioned at a predetermined location or orientation relative to the first optical axis 60a of the first eye, and the second IOL device 110b or the identifiable magnetic field 50b or pole axis of the magnetic field source 50b or the identifiable magnetic field 50b can be oriented relative to the second optical axis 60b of the second eye at a predetermined pitch angle α. Generally, the predetermined pitch angle can be any suitable angle, which can vary from one embodiment to the next. For example, the pitch angle α can be a non-parallel angle relative to the first or second optical axes 60a or 60b, an obtuse angle, or an acute angle. Moreover, as described below in more detail, the pitch angle can be 0°, such that a magnetic field component of the identifiable magnetic field 50b is substantially parallel to the second optical axis 60b.

Furthermore, the identifiable magnetic field 50b can be oriented such that the sensor 140a or the controller 130a can distinguish between in-tilt or convergence of the eyes (e.g., when the subject attempts to change focus on from a first object to a second object that is closer to the subject) from co-tilt of the eyes (e.g., when the subject tilts or pivots eyes to focus on an object located peripherally, such as to the left or to the right of the subject). For example, the identifiable magnetic field 50b can be oriented at about 45° relative to the second optical axis 60b (e.g., within less than 1° of the 45°, within less than 2° of the 45°, within less than 5° of the 45°).

It should be appreciated that the identifiable magnetic field 50b can have any suitable orientation relative to the second optical axis 60b. For example, the identifiable magnetic field 50b can be oriented relative to the second optical axis 60b such that convergence of the eyes results in an increased magnitude or changed direction of the magnetic field vector (e.g., Lorentz force vector), which can be distinguishable from the direction of the magnetic field vector sensed by the sensor 140a when the eyes co-tilt, as discussed below in more detail. In other words, the identifiable magnetic field 50b can be oriented such that the detection output received from the sensor 140a can be processed by the controller 130a to distinguish or identify the change in magnitude or direction of the Lorentz force vector of the identifiable magnetic field 50b in a manner that the controller 130a can distinguish convergence or in-tilt of the eyes from co-tilt.

It should be also appreciated that the sensor 140a of the first IOL device 110a can be configured to measure the strength and direction of the magnetic field, to measure the component of the magnetic field in a specific sensitivity direction, or to include multiple (collocated or not) magnetic sensors each of which is configured to measure separately directed components of the magnetic field. In an embodiment, the sensor 140a includes a sensor configured to measure a magnetic field component oriented at 0° relative to the first optical axis 60a. In an embodiment, the sensor 140a includes a sensor configured to measure a magnetic field component oriented at 90° relative to the first optical axis 60a (e.g., in the plane of the first IOL device 110a) directed to or away from the second IOL device 110b. The sensor 140a is mounted or embedded within the first IOL device 110a so that as the first eye tilts, changing the direction of first optical axis 60a and first IOL device 110a, the sensitivity direction of the sensor 140a also changes. Accordingly, the value of a specific directional component of magnetic field measured by the sensor 140a will change based on changes in the tilt of the first eye. It should be further appreciated, that the value of a specific directional component of magnetic field measured by the sensor 140a will also be changed by changes in the direction the magnetic field source 50b, and the accompanying changes in the field at the location of the sensor 140a. Since the magnetic field source 50b is implanted in the second eye (either directly, or indirectly via being mounted in the second IOL device 110b), then field values measured by the sensor 140a will change based on changes in the tilt of the second eye. Accordingly, field values measured by the sensor 140a will change based on changes in the tilt of both the first eye and the second eye.

It should be also appreciated that the second IOL device 110b can include multiple magnets that can establish multiple identifiable magnetic fields. Moreover, a single identifiable magnetic field oriented at an acute or obtuse angle relative to the second optic axis 60b can be represented by superpositioning two or more identifiable magnetic fields established by multiple magnets. Conversely, a single tilted identifiable magnetic field source (e.g., magnetic field source oriented at 45° relative to the second optic axis 60b) can be represented as two magnetic field sources: e.g., an in-plane field source $m_\parallel$ oriented parallel to the plane of the IOL (i.e., orthogonal to the optical axis 60b), and an out-of-plane field source $m_\perp$ oriented perpendicular to the plane of the IOL (i.e., along the optical axis 60b). The sensor 140a can be configured to measure magnetic field at a specified angle relative to the optical axis 60a. In an embodiment, one or more sensors 140a can measure an in-plane magnetic field component $b_\parallel$ and an out-of-plane magnetic field component $b_\perp$. For dipole-dominated magnetic fields, the relative magnetic field components measured by sensor 140a can be written in matrix form as $$\begin{pmatrix} b_\perp \\ b_\parallel \end{pmatrix} = \begin{pmatrix} B_{\perp\perp} & B_{\perp\parallel} \\ B_{\parallel\perp} & B_{\parallel\parallel} \end{pmatrix} \begin{pmatrix} m_\perp \\ m_\parallel \end{pmatrix}$$

For a magnetic field generated by a dipole source, the dimensionless field b at a given distance depends on the orientation of the source, $\hat{m}$, and that of the location $\hat{r}$ at which the field is being measured:

$$b = 3(\hat{m}\cdot\hat{r})\hat{r} - \hat{m}$$

In this case, the four matrix elements are (using $\theta_1$ as the tilt of the first eye and $\theta_2$ for the second eye):

$$B_{\perp\perp} = 2\sin\theta_1 \sin\theta_2 - \cos\theta_1 \cos\theta_2$$

$$B_{\perp\|} = 2\sin\theta_1 \cos\theta_2 + \cos\theta_1 \sin\theta_2$$

$$B_{\|\perp} = 2\cos\theta_1 \sin\theta_2 + \sin\theta_1 \cos\theta_2$$

$$B_{\|\|} = 2\cos\theta_1 \cos\theta_2 - \sin\theta_1 \sin\theta_2$$

Since eye rotations are small, we can usefully approximate these relations as:

$$B_{\perp\perp} = -1$$

$$B_{\perp\|} = 2\theta_1 + \theta_2$$

$$B_{\|\perp} = 2\theta_2 + \theta_1$$

$$B_{\|\|} = 2$$

The dominant matrix elements; $B_{\perp\perp}$, the perpendicular field due to a perpendicular source and $B_{\|\|}$, the parallel field due to a parallel source are not sensitive to eye tilts. However, the cross terms, $B_{\perp\|}$, the perpendicular field due to a parallel source and $B_{\|\perp}$, the parallel field due to a perpendicular source are sensitive to eye tilts, depending on both of them. Neither one of these elements, by itself, is capable of distinguishing between vergence and co-tilt, but in combination, they are.

Vergence: $\phi = \theta_2 - \theta_1 = B_{\|\perp} - B_{\perp\|}$

Co-Tilt: $\psi = \frac{1}{2}(\theta_1 + \theta_2) = \frac{1}{6}(B_{\|\perp} + B_{\perp\|})$ In an embodiment, the magnetic field source 50b in the second eye includes two magnetic field sources, one with dipole moment $m_\perp$ oriented perpendicular to the plane of the second IOL (i.e., along the optical axis 60b), and the other with dipole moment $m_\|$ oriented parallel to the plane of the IOL (i.e., orthogonal to the optical axis 60b). In such an embodiment, the sensor 140a in the first eye is configured to measure magnetic fields in two orthogonal directions, measuring an in-plane magnetic field component $b_\|$ and an out-of-plane magnetic field component $b_\perp$. As described above, in this embodiment, the cross terms $B_{\perp\|}$ and $B_{\|\perp}$ can be determined, and used to determine the vergence between the two eyes; if desired, these can also determine the co-tilt. In some situations (e.g., when magnetic dipole moments $m_\perp$ and $m_\|$ are produced with permanent magnets), the measured field component $b_\|$ may include contributions from both $m_\perp$ and $m_\|$, likewise for $b_\perp$. In such situations, the controller can separate these contributions (e.g., distinguish $B_{\|\|}$ from $B_{\perp\|}$, and distinguish $B_{\perp\|}$ from $B_{\perp\perp}$) by using the fact that $B_{\|\|}$ and $B_{\perp\perp}$ are insensitive to eye tilts (and hence will remain substantially constant in time); changes in measured $b_\|$ or $b_\perp$ values correspond to the $B_{\|\perp}$ and $B_{\perp\|}$ terms. In other embodiments, such potential ambiguities can be avoided by use of time variable magnetic field sources (e.g., pulsed electromagnets), such that $m_\perp$ and $m_\|$ are active at different times.

In another embodiment, the magnetic field source 50b in the second eye can be tilted at an angle α from the optical axis 60b. In this embodiment, the sensor 140a can be configured to measure the magnetic field component along a direction generally perpendicular to the magnetic field source 60b, i.e., at an angle (α-90° from optical axis 60a, pointing back towards the second eye. In this situation, the proportionality B between the detected field and the dipole source is:

$$B = -0.5\sin\phi - 1.5\sin 2\alpha \cos\phi - 1.5\cos 2\alpha \sin 2\psi$$

In general, this depends upon both the vergence $\phi$ and the co-tilt $\psi$. However, by properly selecting the tilt angle α to be 45 degrees, the detected signal no longer depends on co-tilt, and can be directly used to determine vergence.

$$B = -0.5\sin\phi - 1.5\cos\phi \approx -1.5 - 0.5\phi$$

The controller 130a including the control electrical circuitry thereof can distinguish between co-tilt and in-tilt (vergence) using the above methodology and formulas. It is apparent that a similar arrangement of components (i.e., magnetic field source 50a in the first eye and sensor 140b in the second eye) can be employed to enable a controller 130b (located for example in the second eye) to independently determine vergence and/or co-tilt. It is also apparent that, for the above embodiment with field source and sensor oriented at 45° from the optical axes, the magnetic field source 50a can be oriented perpendicular to the sensitivity direction of sensor 140a, while the sensitivity direction of sensor 140b can be oriented perpendicular to magnetic field source 50b; such alignments may be advantageous for signal to noise purposes.

As described above, components of the first IOL device 110a can be oriented at a predetermined angle relative to an optical axis 60a of the first eye. For example, the sensor 140a can be positioned such that when the eyes converge (e.g., in a manner representative of the eyes changing focus to a closer object), the sensor 140a pivots with the eye to be more sensitive to the identifiable magnetic field 50b (as compared before eye movement); when the eyes co-tilt in a first direction (e.g., in a manner representative of the eyes looking to the left (as shown in FIG. 5C)), the sensor 140a moves together with the eye and can be aligned closer and be more sensitive to the second, south pole of the identifiable magnetic field 50b than to the north pole; when the eyes co-tilt in a second direction (e.g., in a manner representative of the eyes looking to the right), the sensor 140a can move with the eye and can be aligned closer to and be more sensitive to the north pole of the identifiable magnetic field 50b (as compared before eye movement (as shown in FIG. 5D)).

In any event, in an embodiment, when the controller 130a receives the detection output generated by the sensor 140a, the controller 130a can identify vergence rotation between the eyes (e.g., convergence) and can distinguish the vergence rotation from co-tilt of the eyes. Moreover, the controller 130a can direct the first IOL device 110a to change the focal length from the first focal length to the second focal length at least partially based on the detection output(s) of the sensor 140a, which can correspond to vergence rotation between the eyes.

As mentioned above, in the illustrated embodiment, the magnetic field source 150b can be included in the second IOL device 110b that can be located in the subject's second eye. For example, the second IOL device 110b can include a second lens 111b that can be similar to or the same as the first lens 111a of the first IOL device 110a. In an embodiment, the second IOL device 110b also can include an additional or second controller (not shown) that can switch or direct switching of the second IOL device 110b between two or more focal lengths. Moreover, the controller 130a can communicate with the second controller and can send the focal length indication thereto. For example, the controller 130*a* can be operably connected to a first communication device (not shown), and the second controller can be connected to a second communication device (not shown) that can be in communication with or configured to communicate with the first communication device. In other words, the first and second communication devices can be operably coupled.

For example, via communication between the first and second communication devices, the controller 130*a* can send to the additional, second controller the controller data. Generally, controller data can include any data or any number of suitable parameters. In an embodiment, the controller data can include information or instructions for switching the first lens 111*a* or the second lens 111*b* to the first focal length or to the second focal length (e.g., the controller data can associated with selected focal length for the first lens 111*a* or for the second lens 111*b*). Additionally or alternatively, the controller data can include or can be associated with the detection output of the sensor 140*a*.

In an embodiment, the first IOL device 110*a* or the second IOL device 110*b* can include additional or alternative sensors that can detect eye movement in a manner that can aid the controller 130*a* or the additional, second controller to identify or determine vergence rotation between the eyes. For example, the first IOL device 110*a* or second IOL device 110*b* can include one or more accelerometers or gyroscopes. More specifically, outputs generated by the accelerometers or gyroscopes can indicate the direction of rotation or tilting for the first or second eyes.

In an embodiment, the direction of tilting or rotation detected or sensed by the accelerometers or gyroscopes in the first eye can be communicated to and compared with the direction of tilting or rotation detected or sensed by the accelerometers or gyroscopes in the second eye. For example, the controller 130*a* can communicate with the additional, second controller (as described above) and can send controller data thereto (e.g., the controller data can include processed or unprocessed output from the accelerometers or from the gyroscopes). The controller 130*a* or the additional, second controller can distinguish co-tilting or the eyes are tilting in the same direction from vergence rotation or the eyes are tilting in different directions (e.g., to focus on an object closer or farther away from previously viewed object). Moreover, based at least partially on the outputs received from the accelerometers or gyroscopes in the first and second eyes, the controller 130*a* or the additional, second controller can determine the focal lengths for the first lens 111*a* or for the second lens 111*b*.

In an embodiment, the controller 130*a* or the second controller can use the detection outputs from the accelerometers or gyroscopes to cross-check or verify the determination on the change in vergence between the eyes, which can be based on the output from the sensor 140*a*. Conversely, the controller 130*a* or the second controller can use the detection outputs from the sensor 140*a* to cross-check or compare the determination or identification of the vergence rotation between the eyes, which can be based on the output from the accelerometers or gyroscopes. Moreover, in an embodiment, the accelerometers or gyroscopes can be initially or periodically calibrated (e.g., based on the detection outputs from the sensor 140*a*) to adjust for noise, drift, other errors, etc.

Figure 5B:
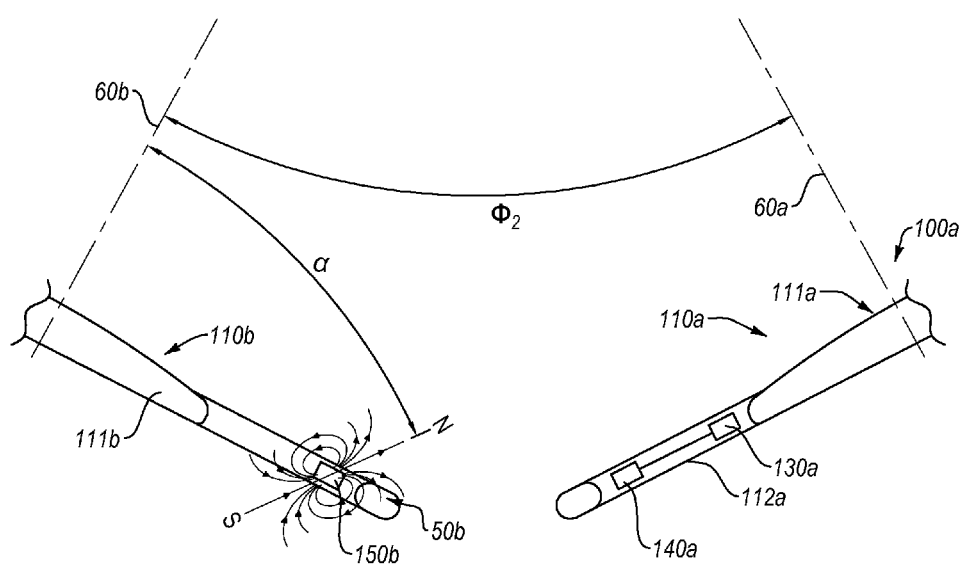
FIG. 5B is a schematic top view of the IOL system of FIG. 5A in which the IOL devices are oriented by the subject's eyes at a second vergence therebetween according to an embodiment.
Figure 5C:
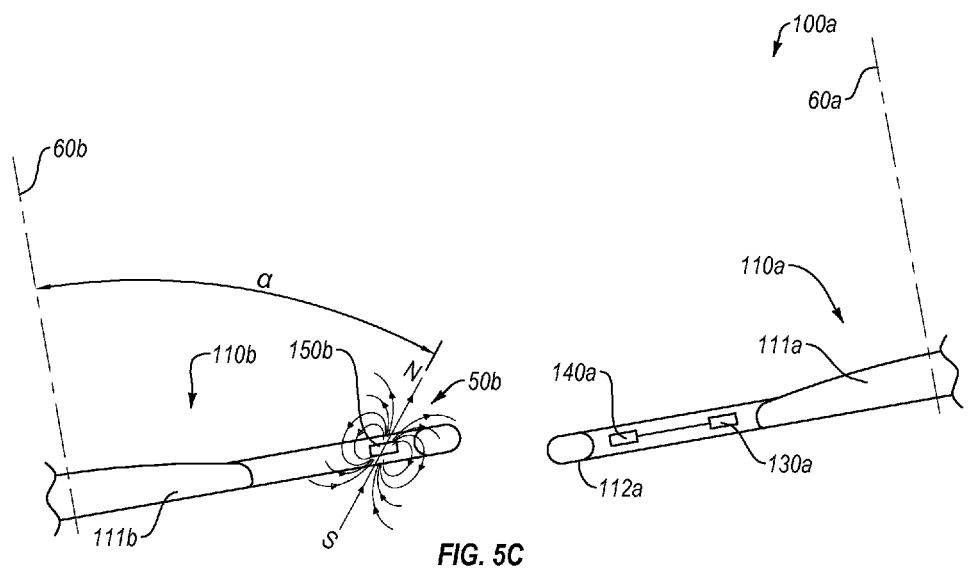
FIG. 5C is a schematic top view of the IOL system of FIG. 5A in which the IOL devices are oriented by the subject's eyes co-tilted in a first direction according to an embodiment.
Figure 5D:
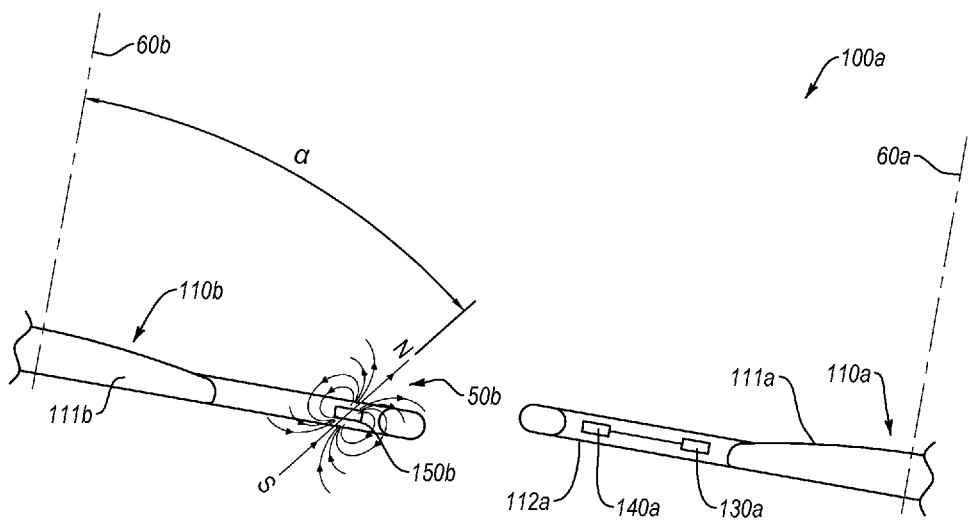
FIG. 5D is a schematic top view of the IOL system of FIG. 5A in which the IOL devices are oriented by the subject's eyes co-tilted in a second direction according to an embodiment.

FIG. 5B shows the first IOL device 110*a* and second IOL device 110*b* and corresponding eyes (not shown) tilted compared with the respective orientations thereof shown in FIG. 5A responsive to corresponding convergence of the first and second eyes of the subject. In particular, for example, the first IOL device 110*a* can remain substantially stationary relative to first optical axis 60*a*, and the second IOL device 110*b* can remain substantially stationary relative to the second optical axis 60*b*. Hence, as the first eye tilts toward or away from the second eye, the first IOL device 110*a* can correspondingly tilt toward the second IOL device 110*b* (e.g., vergence rotation between the first and second eyes can produce a corresponding change in relative orientations or positions of the first IOL device 110*a* and second IOL device 110*b*). In particular, the first and second eyes can converge to form the second angle $\phi_2$ between the respective first and second optical axes 60*a*, 60*b* thereof, and the first IOL device 110*a* and second IOL device 110*b* can correspondingly converge together.

As described above, for example, when the first IOL device 110*a* and second IOL device 110*b* converge, the sensor 140*a* can be reoriented or repositioned relative to the magnetic field source 150*b* and relative to the identifiable magnetic field 50*b* established thereby. More specifically, for example, the identifiable magnetic field 50*b* and the sensor 140*a* can be reoriented relative to each other such that the sensor 140*a* can generate an output related to a change in the direction of the magnetic field vector or magnitude thereof. Furthermore, at least partially based on the output from the sensor 140*a*, the controller 130*a* can distinguish vergence rotation between the eyes (e.g., convergence of the eyes) from co-tilt of the eyes, as described above.

Furthermore, as shown in FIG. 5C, when the eyes tilt in the same direction or co-tilt towards the left, such that the respective first and second optical axes 60*a*, 60*b* thereof are generally parallel to each other, while the first IOL device 110*a* and the second IOL device 110*b* remain generally parallel to one another, the angular position of sensor 140*a* relative to the polar axis of magnetic field source 50*b* changes. The sensor 140*a* and the identifiable magnetic field 50*b* are reoriented, such that the relative position of the sensor 140*a* changes from being closer to the north pole of the identifiable magnetic field 50*b* to being closer to the south pole of the identifiable magnetic field 50*b*. Hence, for example, the detection output from the sensor 140*a* can correspond to a detected change in the direction of the magnetic field vector, and the controller 130*a* can correlate the detection output from the sensor 140*a* to the co-tilt of the eyes.

Alternatively, as shown in FIG. 5D, the eyes can co-tilt towards the right, such that while the first IOL device 110*a* and the second IOL device 110*b* remain generally parallel to one another, the angular position of sensor 140*a* relative to the polar axis of magnetic field source 50*b* changes. For example, after repositioning or reorientation of the sensor 140*a* and of the identifiable magnetic field 50*b* (responsive to co-tilt of the eyes to the right), the detection output from the sensor 140*a* can correspond to a detected change in the magnetic field vector, and the controller 130*a* can correlate the detection output from the sensor 140*a* to the co-tilt of the eyes. In any event, the first IOL device 110*a* and second IOL device 110*b* can be positioned or oriented relative to the first optical axis 60*a* and second optical axis 60*b* such that the detection output from the sensor 140*a* can be correlated by the controller 130*a* to distinguish vergence rotation (e.g., convergence or in-tilt of the eyes) from the co-tilt of the eyes.

Figure 6A:
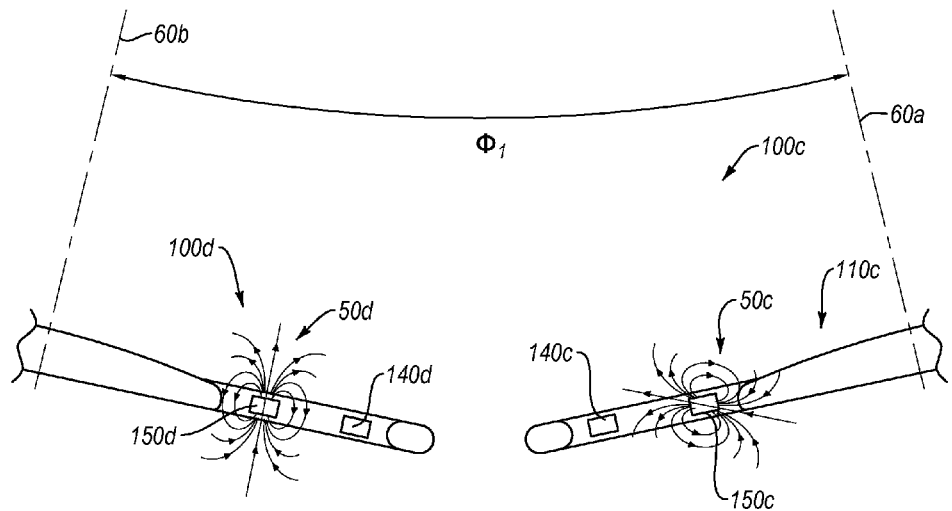
FIG. 6A is a schematic top view of an IOL system that includes two IOL devices oriented by the subject's eyes at a first vergence therebetween according to another embodiment.
Figure 6B:
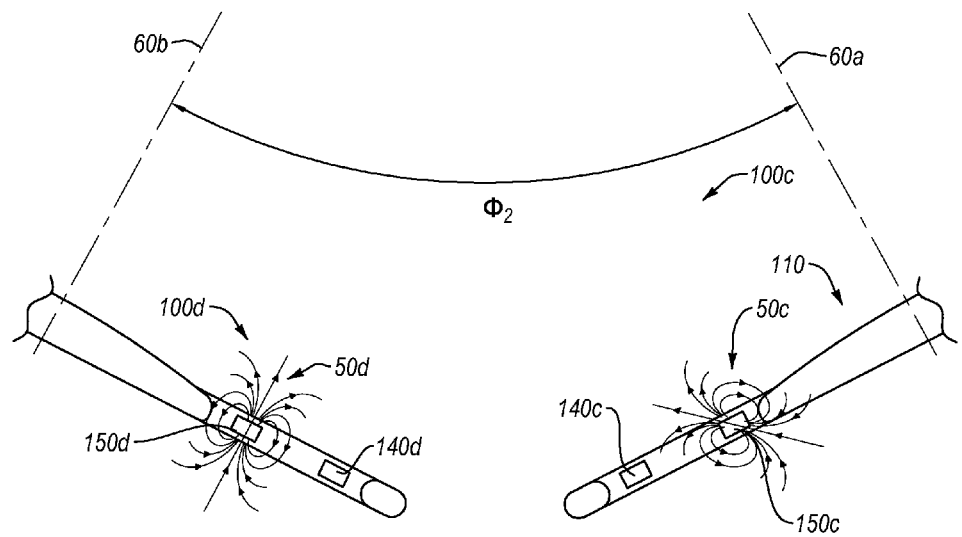
FIG. 6B is a schematic top view of the IOL system of FIG. 6A in which the IOL devices are oriented by the subject's eyes at a second vergence therebetween according to an embodiment.

As described above, the IOL system can include multiple identifiable fields and multiple corresponding sensors that can detect relative change in position or orientation therebetween. FIGS. 6A and 6B illustrate an IOL system 100*c* that includes a first IOL device 110*c* and a second IOL device 110*d* and establishes multiple identifiable magnetic fields, according to an embodiment. In particular, FIG. 6A illustrates the first IOL device 110*c* and the second IOL device 110*d* at first respective locations or orientations relative to each other when the subject's eyes (not shown) focus or attempt to focus at a first focal length, such that the respective first and second optical axes 60*a*, 60*b* of the first and second eye define the first angle $\phi_1$ therebetween. For example, the first IOL device 110*c* and the second IOL device 110*d* can be substantially fixed relative to the first and second optical axes 60*a*, 60*b* of the subject's eyes. FIG. 6B illustrates the first IOL device 110*c* and the second IOL device 110*d* at second respective locations or orientations relative to each other when the subject is attempting to focus or focusing the eyes (not shown) at a second focal length, such that the first optical axis the 60*a* and second optical axis 60*b* define the second angle $\phi_2$ therebetween. The following describes the IOL system 100*c* as the subject in-tilts and out-tilts the eyes (e.g., such that vergence rotation between the eyes tilts or pivots the first and second optical axis the 60*a*, 60*b* between defining first angle $\phi_1$ and second angle $\phi_2$).

Except as otherwise described herein, the IOL system 100*c* and its elements and components can be similar to or the same as any of the IOL systems 100, 100*a* (FIGS. 1-5D) and their corresponding elements and components. For example, the first IOL device 110*c* can include a first sensor 140*c* and a first controller (not shown) including control electrical circuitry, which can be similar to or the same as the sensor 140*a* and controller 130*a* of the first IOL device 110*a* (FIGS. 5A-5D). Similarly, the second IOL device 110*d* can include a second sensor 140*d* and a second controller (not shown) including control electrical circuitry, which also can be similar to or the same as the sensor 140*a* and controller 130*a* of the first IOL device 110*a* (FIGS. 5A-5D).

In the illustrated embodiment, the first IOL device 110*c* includes a first field source 150*c* that can establish a first identifiable magnetic field 50*c*, and the second IOL device 110*d* includes a second field source 150*d* that can establish a second identifiable magnetic field 50*d*. Generally, the first identifiable magnetic field 50*c* and second identifiable magnetic field 50*d* can have any suitable orientation relative to the first optical axis 60*a* or to the second optical axis 60*b* of the first eye and second eye. In an embodiment, the first identifiable magnetic field 50*c* can be oriented at about 90° relative to the first optical axis 60*b*, and the second identifiable magnetic field 50*d* can be oriented generally parallel to the second optical axis 60*b*, or vice versa. Moreover, the first identifiable magnetic field 50*c* and second identifiable magnetic field 50*d* can have any suitable orientation relative to each other. For example, the first identifiable magnetic field 50*c* and the second identifiable magnetic field 50*d* can be oriented generally perpendicular to each other (e.g., when the first and second optical axes 60*a*, 60*b* are relatively oriented to define the first angle $\phi_1$ or the second angle $\phi_2$). In an embodiment, the first identifiable magnetic field 50*c* or the second identifiable magnetic field 50*d* can be oriented generally parallel to an axis extending between the eyes.

As described above, the first sensor 140*c* and second sensor 140*d* can detect change in the position or orientation of the respective second identifiable magnetic field 50*d* and first identifiable magnetic field 50*c* as the eyes together with the first IOL device 110*c* and second IOL device 110*d* converge or diverge. For example, the first sensor 140*c* can sense the first identifiable magnetic field 50*d* and can generate a first detection output as the second identifiable magnetic field 50*d* and the first sensor 140*c* move relative to each other. In an embodiment, the first sensor 140*c* can detect a changed component of the second identifiable magnetic field 50*d* (e.g., in a direction that is substantially perpendicular to the dominant component of the second identifiable magnetic field 50*d*). For example, the first detection output of the first sensor 140*c* can at least partially correspond to the vergence rotation between the eyes. The second sensor 140*d* can detect a changed component of the first identifiable magnetic field 50*c* (e.g., in a direction that is substantially perpendicular to the dominant component of the first identifiable magnetic field 50*c*), which can at least partially correspond to the vergence rotation between the eyes. As such, a second detection output of the second sensor 140*d* also can at least partially correspond to a change in the vergence between the eyes or to vergence rotation. As described below in more detail, the first or second controllers can compare the first and second detection outputs to determine the vergence rotation between the eyes.

In one or more embodiments, the first and second controllers can receive the corresponding first and second detection outputs from the respective first and second sensors 140*c*, 140*d* and can process the detection outputs to generate controller data based thereon (e.g., can identify or determine vergence rotation between the eyes or can distinguish vergence rotation from co-tilt of the eyes). In an embodiment, the controller data can include the first and second detection outputs. Moreover, the first controller can send the controller data to the second controller (e.g., via corresponding communication devices), or vice versa. Hence, for example, the first or the second controller can receive first and second detection outputs. Furthermore, in an embodiment, the first or second controller can compare the first and second detection outputs to determine the vergence rotation between the eyes (e.g., to distinguish convergence, divergence, and co-tilt of the eyes).

In an embodiment, after determining the vergence rotation between the eyes, the first or second controller can determine the suitable or selectable focal length for the first IOL device 110*c* or for the second IOL device 110*d*. For example, as described above, the first IOL device 110*c* or second IOL device 110*d* can include one or more switchable lenses that can be switched between two or more focal lengths (e.g., the first or second controllers can switch or direct switching of the switchable lenses). The first controller can direct the first IOL device 110*c* to switch to a first focal length or to a second focal length based on the determined vergence rotation. Analogously, the second controller can direct the second IOL device 110*d* to switch to a first focal length or to a second focal length based on the determined vergence rotation. In an embodiment, the first controller can send controller data to the second controller (or vice versa), and the controller data can include the determined vergence rotation or change in the vergence between the eyes or the suitable or selected focal length for the first IOL device 110*c* or second IOL device 110*d*.

Figure 7A:
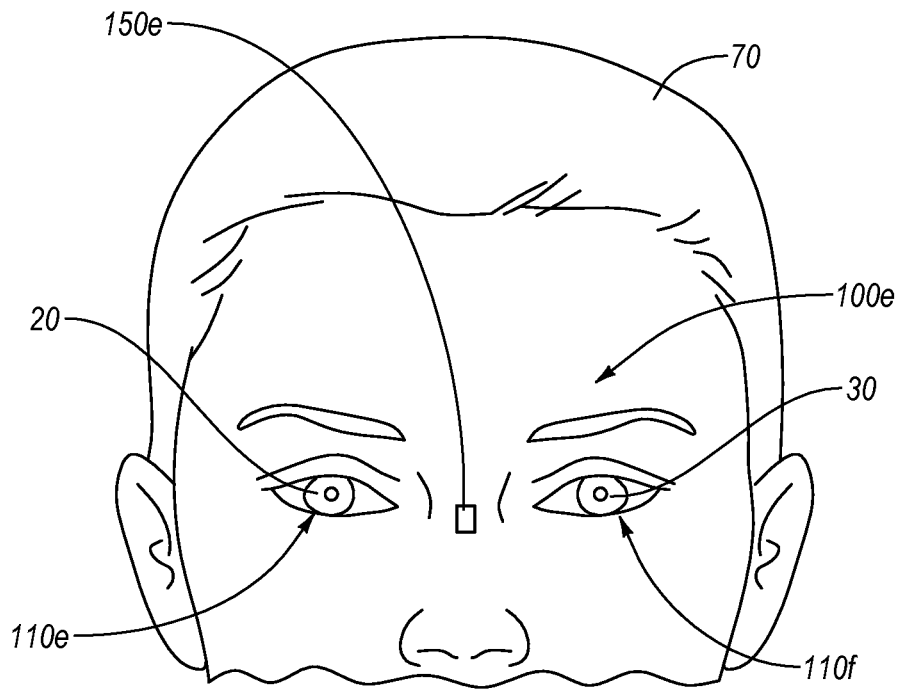
FIG. 7A is a schematic view of an IOL system that includes two IOL devices oriented by the subject's eyes at a first vergence therebetween according to yet another embodiment.
Figure 7B:
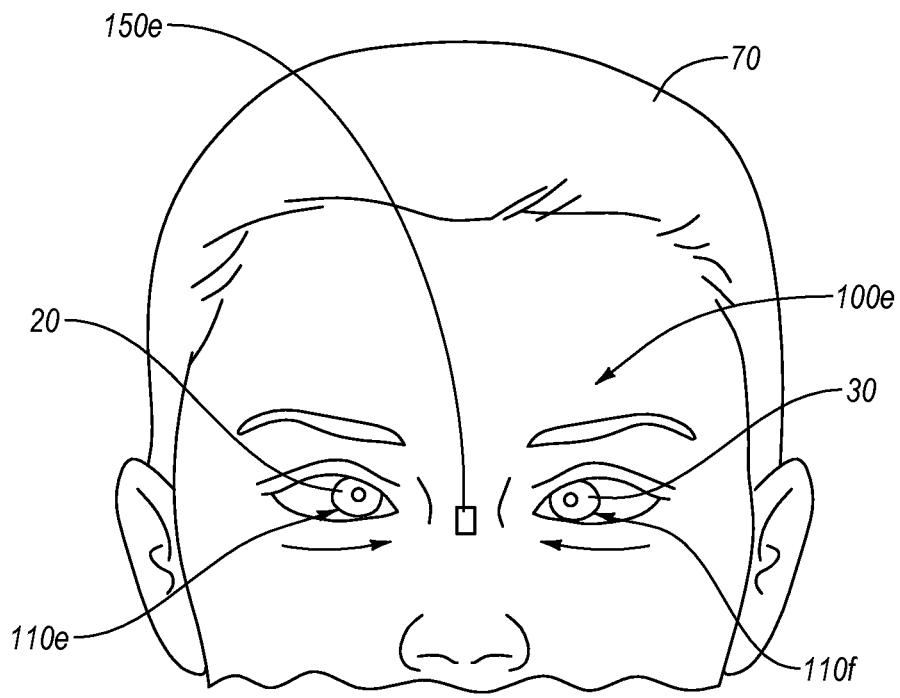
FIG. 7B is a schematic view of the IOL system of FIG. 7A in which the IOL devices are oriented by the subject's eyes at a second vergence therebetween.

As described above, in an embodiment, the IOL system can include a field source positioned externally to the subject's eyes. FIGS. 7A and 7B illustrate an IOL system 100*e* that includes IOL devices 110*e* and 110*f* located in the respective first and second eyes 20, 30 of a subject 70 and a magnetic field source 150*e* positioned externally to the first and second eyes 20, 30, according to an embodiment. In particular, FIG. 7A illustrates the first and second eyes 20, 30 of the subject 70 at first tilt, positioned to focus on first object located at first distance from the subject 70. FIG. 7B illustrates the first and second eyes 20, 30 at second tilt, positioned to focus on second object located at second distance from the subject 70. The following describes the IOL system 100e as the subject 70 tilts or pivots the first and second eyes 20, 30 between the first and second tilt positions (e.g., the vergence change between the eyes tilts the first and second eyes 20, 30 between the first and second tilt positions).

In an embodiment, the magnetic field source 150e can establish an identifiable magnetic field that can be detected by one or more sensors in the first IOL device 110e or in the second IOL device 110f, as the subject 70 changes tilt of the first and second eyes 20, 30 between the first tilt and the second tilt. Generally, the magnetic field source 150e can establish the identifiable magnetic field at any suitable angle relative to the first/or second eyes 20, 30 or to the optical axes thereof. For example, similar to the IOL system 100a (FIGS. 5A-5D), the magnetic field source 150e can establish the identifiable magnetic field that is oriented at approximately 45° angle relative to the optical axis of the second eye 30 when the first and second eyes 20, 30 are at the first tilt therebetween. In contrast to the IOL system 100a (FIGS. 5A-5D), the magnetic field established by the magnetic field source 150e can remain substantially stationary relative to the subject 70 (e.g., relative to the head of the subject 70). In an embodiment, movement or tilting of the first eye 20 or the second eye 30 can produce a corresponding relative movement or tilting between the magnetic field source 150e and the sensors of the IOL system 100e (e.g., the identifiable magnetic field established by the magnetic field source 150e can remain stationary relative to the head of the subject, and the sensors of the IOL system 100e can move together with the first and second eyes 20, 30, such as during vergence rotation therebetween).

In an embodiment, the first IOL device 110e can include a first sensor. As the first IOL device 110e pivots or tilts together with the first eye 20, the first sensor can detect a changed component of the identifiable magnetic field in a direction that is substantially perpendicular to the direction of the dominant component of the identifiable magnetic field. Furthermore, the second IOL device 110f can include a second sensor. As the second IOL device 110f pivots or tilts together with the second eye 30, the second sensor can detect a changed component of the identifiable magnetic field in a direction that is substantially perpendicular to the direction of the dominant component of the identifiable magnetic field.

As described above, the first IOL device 110e or the second IOL device 110f can include one or more controllers including control electrical circuitry operably coupled to the respective first and second sensors. For example, the first IOL device 110e can include a first controller operably coupled to the first sensor and configured to receive a first detection output therefrom (e.g., the first sensor can generate the first detection output based on the detected change in a component of the identifiable magnetic field). Similarly, the second IOL device 110f can include a second controller operably coupled to the second sensor and configured to receive a second detection output therefrom (e.g., the second sensor can generate the second detection output based on the detected change in a component of the identifiable magnetic field in a similar manner as described above).

In an embodiment, the first controller can be operably coupled to or can be in communication with the second controller. For example, the first controller can be operably coupled to a first communication device and the second controller can be operably coupled to the second communication device, and the first and second communication devices can be configured to transmit data therebetween. Hence, the first controller can send controller data (which can include the detection output from the first sensor or determination of focal length) to the second controller. Additionally or alternatively, the second controller can send controller data (which can include the detection output from the second sensor or determination of focal length) to the first controller. Moreover, the first controller or the second controller is configured to distinguish vergence rotation from co-tilt rotation of the first and second eyes 20, 30 based on the first and second detection outputs.

As described above, the first or second controller also is adapted to determine a suitable or selectable focal length for one or more switchable lenses. For example, the first IOL device 110e can include a first switchable lens that can be switched between two or more focal lengths. Alternatively or additionally, the second IOL device 110f can include a second switchable lens that can be switched between two or more focal lengths. Hence, the first controller or second controller can direct or switch the first switchable lens or second switchable lens based on the first and second detection outputs.

In an embodiment, the IOL system 100e can include multiple magnetic field sources that can generate multiple corresponding identifiable magnetic fields. Generally, each of the multiple magnetic field sources can be oriented relative to the first eye 20 or second eye 30 (e.g., as measured when the first and second eyes 20, 30 are at the first tilt therebetween). Likewise, multiple magnetic field sources can be oriented relative to one another at any number of suitable angles. For example, a first identifiable magnetic field can be oriented at a first predetermined angle relative to the optical axis of the first eye 20, and a second identifiable magnetic field can be oriented at a second predetermined angle relative to the second eye 30 (e.g., when the first and second eyes 20, 30 are at the tilt).

The magnetic field source 150e or additional or alternative magnetic field sources can be generally fixedly positioned relative to the subject 70 with any number of suitable mechanisms or configurations. For example, the magnetic field source 150e can be implanted near the first eye 20 or second eye 30 of the subject 70 (e.g., near or on the bridge of the nose of the subject 70). Additionally or alternatively, the magnetic field source 150e can be removably positioned on or secured to the subject 70 (e.g., with an adhesive, on a wearable object, such as glasses, etc.). In any embodiment, the magnetic field source 150e can be generally stationary relative to the head of the subject 70, such that tilting or pivoting of the first and second eyes 20, 30 can result in relative movement between the first eye 20 and the identifiable magnetic field and between the second eye 30 and identifiable magnetic field.

In another embodiment, the locations of field sources and field sensors described in conjunction with FIG. 7, can be generally reversed. In such an embodiment, the IOL system 110e and the IOL system 110f can include implanted or embedded magnetic field sources, while one or more magnetic field sensors can be generally fixedly positioned relative to the subject 70 (e.g., in locations discussed above with reference to 150e). In this embodiment, the orientations of the magnetic fields change as the eyes tilt, resulting in changed values of magnetic field detected by the fixedly positioned sensor(s). A controller (e.g., a controller external to the IOLs) can receive the signals from the field sensor(s) and determine the tilts of one or both eyes. In particular, the controller can compare tilt values from both eyes to thereby determine vergence, and can distinguish vergence from co-tilt. The controller can then be operatively coupled (e.g., by wireless communication) with controllers in each IOL, which then direct focal length changes of their respective IOL optics. In this embodiment, each IOL only needs a communicative receiver, but does not necessarily require a transmitter.

It will be understood that a wide range of hardware, software, firmware, or virtually any combination thereof can be used in the controllers described herein. In one embodiment, several portions of the subject matter described herein can be implemented via Application Specific Integrated Circuits (ASICs), Field Programmable Gate Arrays (FPGAs), digital signal processors (DSPs), or other integrated formats. However, some aspects of the embodiments disclosed herein, in whole or in part, can be equivalently implemented in integrated circuits, as one or more programs running on one or more processors (e.g., as one or more programs running on one or more microprocessors), as firmware, or as virtually any combination thereof. In addition, the reader will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution.

In a general sense, the various embodiments described herein can be implemented, individually and/or collectively, by various types of electro-mechanical systems having a wide range of electrical components such as hardware, software, firmware, or virtually any combination thereof; and a wide range of components that can impart mechanical force or motion such as rigid bodies, spring or torsional bodies, hydraulics, and electro-magnetically actuated devices, or virtually any combination thereof. Consequently, as used herein "electro-mechanical system" includes, but is not limited to, electrical circuitry operably coupled with a transducer (e.g., an actuator, a motor, a piezoelectric crystal, etc.), electrical circuitry having at least one discrete electrical circuit, electrical circuitry having at least one integrated circuit, electrical circuitry having at least one application specific integrated circuit, or a microprocessor configured by a computer program which at least partially carries out processes and/or devices described herein), electrical circuitry forming a memory device (e.g., forms of random access memory), electrical circuitry forming a communications device (e.g., a modem, communications switch, or optical-electrical equipment), and any non-electrical analog thereto, such as optical or other analogs.

In a general sense, the various aspects described herein which can be implemented, individually and/or collectively, by a wide range of hardware, software, firmware, or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). The subject matter described herein can be implemented in an analog or digital fashion or some combination thereof.

The herein described components (e.g., steps), devices, and objects and the discussion accompanying them are used as examples for the sake of conceptual clarity. Consequently, as used herein, the specific exemplars set forth and the accompanying discussion are intended to be representative of their more general classes. In general, use of any specific exemplar herein is also intended to be representative of its class, and the non-inclusion of such specific components (e.g., steps), devices, and objects herein should not be taken as indicating that limitation is desired.

With respect to the use of substantially any plural and/or singular terms herein, the reader can translate from the plural to the singular and/or from the singular to the plural as is appropriate to the context and/or application. The various singular/plural permutations are not expressly set forth herein for sake of clarity.

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected," or "operably coupled," to each other to achieve the desired functionality, and any two components capable of being so associated can also be viewed as being "operably couplable," to each other to achieve the desired functionality. Specific examples of operably couplable include but are not limited to physically mateable and/or physically interacting components and/or wirelessly interactable and/or wirelessly interacting components and/or logically interacting and/or logically interactable components.

In some instances, one or more components can be referred to herein as "configured to." The reader will recognize that "configured to" or "adapted to" are synonymous and can generally encompass active-state components and/or inactive-state components and/or standby-state components, unless context requires otherwise.

While particular aspects of the present subject matter described herein have been shown and described, it will be apparent that, based upon the teachings herein, changes and modifications can be made without departing from the subject matter described herein and its broader aspects and, therefore, the appended claims are to encompass within their scope all such changes and modifications as are within the true spirit and scope of the subject matter described herein. Furthermore, it is to be understood that the invention is defined by the appended claims. In general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood that if a specific number of an introduced claim recitation is intended, such an intent will be explicitly recited in the claim, and in the absence of such recitation no such intent is present. For example, as an aid to understanding, the following appended claims can contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense the convention (e.g., "a system having at least one of A, B, or C" would include but not be limited to systems that have A alone, B alone, C alone, A and B together, A and C together, B and C together, and/or A, B, and C together, etc.). Virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

With respect to the appended claims, any recited operations therein can generally be performed in any order. Examples of such alternate orderings can include overlapping, interleaved, interrupted, reordered, incremental, preparatory, supplemental, simultaneous, reverse, or other variant orderings, unless context dictates otherwise. With respect to context, even terms like "responsive to," "related to," or other past-tense adjectives are generally not intended to exclude such variants, unless context dictates otherwise.

While various aspects and embodiments have been disclosed herein, the various aspects and embodiments disclosed herein are for purposes of illustration and are not intended to be limiting, with the true scope and spirit being indicated by the following claims.

What is claimed is:

1. An intraocular lens system, comprising:
a magnetic field source sized and configured to be placed in a first eye of a subject, the magnetic field source configured to establish an identifiable magnetic field having a predetermined orientation relative to the first eye;
an intraocular lens device sized and configured to be placed in a second eye of the subject, the intraocular lens device including:
a switchable lens configured to selectively switch between a first focal length and at least a second focal length that is less than the first focal length;
a sensor disposed in the intraocular lens device, the sensor configured to detect a change in the established identifiable magnetic field corresponding to a vergence rotation between the first eye and the second eye, the sensor further configured to generate one or more detection outputs at least partially based on the detected change;
an additional magnetic field source that is distinct from the sensor and configured to establish an additional identifiable magnetic field, the additional magnetic field source disposed in the intraocular lens device; and
a controller operably coupled to the sensor to receive the one or more detection outputs therefrom, the controller configured to detect the vergence rotation by distinguishing a first portion of the rotation due to the vergence rotation between the first eye and the second eye from a second portion due to a co-tilt rotation of both the first eye and the second eye, the controller including control electrical circuitry configured to direct the switchable lens to selectively switch between the first focal length and the at least a second focal length responsive to the one or more detection outputs.

2. The intraocular lens system of claim 1, further comprising an additional intraocular lens device configured to be placed in the first eye.

3. The intraocular lens system of claim 2, wherein the magnetic field source is mounted to or embedded in the additional intraocular lens device.

4. The intraocular lens system of claim 2, further comprising an additional sensor mounted to or embedded in the additional intraocular lens device.

5. The intraocular lens system of claim 4, wherein the additional magnetic field source has a predetermined orientation relative to the second eye, wherein the additional sensor is configured to detect a change in the additional identifiable magnetic field corresponding to the vergence rotation between the first eye and the second eye, and the additional sensor is configured to generate one or more additional detection outputs at least partially based on the detected change.

6. The intraocular lens system of claim 5, wherein the additional magnetic field source is mounted to or embedded in the intraocular lens device.

7. The intraocular lens system of claim 5, further comprising an additional switchable lens mounted to or embedded in the additional intraocular lens device.

8. The intraocular lens system of claim 7, further comprising an additional controller operably coupled to the additional sensor to receive the one or more additional detection outputs therefrom, the additional controller including additional control electrical circuitry configured to direct the additional switchable lens to selectively switch between a first additional focal length and a second additional focal length responsive to the one or more additional detection outputs.

9. The intraocular lens system of claim 8, further comprising a communication device configured to operably couple the controller and the additional controller.

10. The intraocular lens system of claim 9, wherein the communication device is configured to at least one of transmit to the additional controller data associated with the detection output or to transmit to the controller data associated with the additional detection output.

11. The intraocular lens system of claim 9, wherein the communication device is configured to at least one of transmit to the additional controller data associated with the selected focal length of the switchable lens or transmit to the controller data associated with the selected focal length of the additional switchable lens.

12. The intraocular lens system of claim 1, wherein the additional identifiable magnetic field generally aligned at a predetermined pitch angle relative to the identifiable magnetic field.

13. The intraocular lens system of claim 12, wherein the pitch angle is about 90 degrees.

14. The intraocular lens system of claim 12, wherein the magnetic field source includes a dipole magnetic field component oriented substantially parallel to an optical axis of the first eye, and the additional magnetic field source includes an additional dipole magnetic field component oriented substantially parallel to an axis extending between the first eye and the second eye.

15. The intraocular lens system of claim 12, further comprising:
an additional sensor is configured to detect a change in the additional identifiable magnetic field corresponding to the vergence rotation between the first eye and the second eye, the additional sensor configured to generate one or more additional detection outputs at least partially based on the detected change;
wherein a first detection output of the one or more detection outputs at least partially corresponds to a changed component of the identifiable magnetic field in the direction substantially perpendicular to the direction of the dominant component of the identifiable magnetic field;
wherein a second detection output of the one or more additional detection outputs at least partially corresponds to a changed component of the second identifiable magnetic field in a direction substantially perpendicular to the direction of a dominant component of the additional identifiable magnetic field; and
wherein the controller is configured to distinguish the first portion of the rotation from the second portion of the rotation at least partially based on a comparison of the first detection output and the second detection output.

16. The intraocular lens system of claim 1, wherein the sensor is configured to detect a change corresponding to the vergence rotation by detecting a changed component of the identifiable magnetic field in a direction substantially perpendicular to a direction of a dominant component of the identifiable magnetic field.

17. The intraocular lens system of claim 16, wherein the magnetic field source includes a dipole magnetic field component oriented at about 45 degrees from an optical axis of the first eye.

18. The intraocular lens system of claim 1, wherein the controller is configured to determine an apparent object distance from the vergence rotation and to direct the switchable lens to switch to the first focal length or to the at least a second focal length based on the apparent object distance.

19. The intraocular lens system of claim 1, wherein the sensor is mounted to or embedded in the intraocular lens device.

20. The intraocular lens system of claim 1, wherein the magnetic field source includes a permanent magnet.

21. The intraocular lens system of claim 1, wherein the magnetic field source includes an electromagnet.

22. The intraocular lens system of claim 21, wherein the electromagnet is coupled to the controller, and the control electrical circuitry is configured to direct the electromagnet to establish a pulsed identifiable magnetic field.

23. The intraocular lens system of claim 22, wherein the sensor and the controller are configured to distinguish the pulsed identifiable magnetic field from one or more other magnetic fields.

24. The intraocular lens system of claim 1, wherein the identifiable magnetic field is oriented at a non-parallel angle relative to an optical axis of the first eye.

25. The intraocular lens system of claim 1, wherein the switchable lens includes a switchable diffractive lens.

26. The intraocular lens system of claim 1, wherein the switchable lens includes a variable focus refractive lens.

27. The intraocular lens system of claim 1, wherein the one or more detection outputs include one or more detection signals.

28. The intraocular lens system of claim 1, wherein the controller is configured to distinguish the vergence rotation between the first eye and the second eye from a co-tilt rotation of the first eye and the second eye based on the one or more detection outputs.

29. An intraocular lens system, comprising:
a magnetic field source sized and configured to be placed in a first eye of a subject, the magnetic field source configured to establish an identifiable magnetic field having a predetermined orientation relative to the first eye, the magnetic field includes a dipole magnetic field component oriented at a first angle relative to an optical axis of the first eye;
an additional magnetic field source sized and configured to be placed in a second eye, the additional magnetic field source configured to establish an additional identifiable magnetic field generally aligned at a predetermined pitch angle relative to the identifiable magnetic field, the additional magnetic field includes an additional dipole magnetic field component oriented at a second angle relative to an optical axis of the second eye, and the first angle is different from the second angle;
at least one sensor configured to detect a rotation in the established identifiable magnetic field and the additional identifiable magnetic field corresponding to a vergence rotation between the first eye and the second eye of the subject, the at least one sensor configured to generate one or more detection outputs on the detected change, wherein the at least one sensor is distinct from the additional magnetic field source; and
an intraocular lens device sized and configured to be placed in the second eye of the subject, the intraocular lens including the additional magnetic field source and the at least one sensor disposed therein, the intraocular lens device including,
a switchable lens configured to selectively switch between a first focal length and at least a second focal length that is less than the first focal length; and
a controller operably coupled to the at least one sensor to receive the one or more detection outputs therefrom, the controller configured to detect the vergence rotation by distinguishing a first portion of the rotation due to the vergence rotation between the first eye and the second eye from a second portion due to a co-tilt rotation of both the first eye and the second eye, the controller including control electrical circuitry configured to direct the switchable lens to selectively switch between the first focal length and the second focal length responsive to the one or more detection outputs.

30. The intraocular lens system of claim 29, further comprising a communication device operably coupling the sensor to the controller.

31. The intraocular lens system of claim 29, at least one addition sensor that is configured to be implanted in the first eye or the second eye of the subject.

32. The intraocular lens system of claim 29, wherein the sensor is configured to be removably positioned on the subject.

33. The intraocular lens system of claim 29, further comprising an additional intraocular lens device configured to be placed in the first eye, wherein the magnetic field source is mounted to or embedded in the additional intraocular lens device.

34. The intraocular lens system of claim 33, wherein the additional magnetic field source is mounted to or embedded in the intraocular lens device.

35. The intraocular lens system of claim 34, further comprising an additional sensor configured to be positioned externally to the first eye and the second eye and configured to detect a change in the additional established identifiable magnetic field corresponding to a vergence rotation between the first eye and the second eye, and to generate one or more additional detection outputs at least partially based on the detected change.

36. The intraocular lens system of claim 35, further comprising a communication device operably coupling the additional sensor to the controller.

37. The intraocular lens system of claim 36, wherein the additional intraocular lens device includes an additional switchable lens configured to selectively switch between a first focal length and at least a second focal length that is less than the first focal length.

38. The intraocular lens system of claim 37, further comprising an additional controller to receive the one or more additional detection outputs, the additional controller including additional control electrical circuitry configured to direct the additional switchable lens to selectively switch between the first focal length and the at least a second focal length responsive to the additional detection output.

39. The intraocular lens system of claim 38, wherein the communication device or an additional communication device operably couples the additional sensor to the additional controller.

40. An intraocular lens system, comprising:
a magnetic field source sized and configured to be placed in a first eye of a subject, the magnetic field source configured to establish an identifiable magnetic field having a predetermined orientation relative to the first eye;
an additional magnetic field source sized and configured to be placed in a second eye, the additional magnetic field source configured to establish an additional identifiable magnetic field generally aligned at a predetermined pitch angle relative to the identifiable magnetic field;
an intraocular lens device sized and configured to be placed in a second eye of the subject, the intraocular lens device including:
the additional magnetic field source;
a switchable lens configured to selectively switch between a first focal length and at least a second focal length that is less than the first focal length;

a sensor configured to detect a rotation in the established identifiable magnetic field corresponding to a vergence rotation between the first eye and the second eye, the sensor configured to generate one or more detection outputs at least partially based on the detected change, wherein the sensor is distinct from the additional magnetic field source; and
a controller operably coupled to the sensor to receive the one or more detection outputs therefrom, the controller configured to detect the vergence rotation by distinguishing a first portion of the rotation due to the vergence rotation between the first eye and the second eye from a second portion due to a co-tilt rotation of both the first eye and the second eye, the controller including control electrical circuitry configured to direct the switchable lens to selectively switch between the first focal length and the at least a second focal length responsive to the one or more detection outputs; and
wherein at least one of:
the pitch angle is nonzero; or
the magnetic field source includes a dipole magnetic field component oriented substantially parallel to an optical axis of the first eye, and the additional magnetic field source includes an additional dipole magnetic field component oriented substantially parallel to an axis extending between the first eye and the second eye.

41. The intraocular lens system of claim 40, further comprising:
an additional sensor configured to detect a change in the additional identifiable magnetic field corresponding to the vergence rotation between the first eye and the second eye, the additional sensor configured to generate one or more additional detection outputs at least partially based on the detected change.

42. The intraocular lens system of claim 40, wherein a first detection output of the one or more detection outputs at least partially corresponds to a changed component of the identifiable magnetic field in a direction substantially perpendicular to the direction of a dominant component of the identifiable magnetic field.

43. The intraocular lens system of claim 42, wherein a second detection output of the one or more additional detection outputs at least partially corresponds to a changed component of the second identifiable magnetic field in a direction substantially perpendicular to the direction of the dominant component of the second identifiable magnetic field.

44. The intraocular lens system of claim 43, wherein the controller is configured to distinguish the first portion of the rotation from the second portion of the rotation at least partially based on a comparison of the first detection output and the second detection output.

45. The intraocular lens system of claim 43, wherein the pitch angle is about 90 degrees.

* * * * *